(12) United States Patent
Konofagou et al.

(10) Patent No.: US 9,302,124 B2
(45) Date of Patent: Apr. 5, 2016

(54) SYSTEMS AND METHODS FOR OPENING A TISSUE

(75) Inventors: Elisa E. Konofagou, New York, NY (US); James J. Choi, Englewood, NJ (US); Mark A. Borden, Boulder, CO (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/045,070

(22) Filed: Mar. 10, 2011

(65) Prior Publication Data

US 2011/0295105 A1 Dec. 1, 2011

Related U.S. Application Data

(63) Continuation-in-part of application No. PCT/US2009/056565, filed on Sep. 10, 2009.

(60) Provisional application No. 61/095,942, filed on Sep. 10, 2008, provisional application No. 61/377,586, filed on Aug. 27, 2010.

(51) Int. Cl.
*A61M 37/00* (2006.01)
*A61B 8/00* (2006.01)
*A61B 5/055* (2006.01)
*A61N 7/00* (2006.01)
(Continued)

(52) U.S. Cl.
CPC .................. *A61N 7/00* (2013.01); *A61B 8/0808* (2013.01); *A61B 2019/5236* (2013.01); *A61M 37/0092* (2013.01); *A61N 2007/0039* (2013.01)

(58) Field of Classification Search
CPC ........... A61B 8/481; A61B 2019/5425; A61B 8/0808; A61B 2019/5236; A61K 41/0047; A61K 49/223; A61N 2007/0039; A61N 7/00; A61M 37/0092
USPC .................................. 600/431, 433, 439, 427
See application file for complete search history.

(56) References Cited

U.S. PATENT DOCUMENTS

| 3,598,111 A | 8/1971 | Kahn |
| 4,463,608 A | 8/1984 | Takeuchi et al. |
| 4,777,599 A | 10/1988 | Dorogi et al. |

(Continued)

FOREIGN PATENT DOCUMENTS

| EP | 0 221 409 | 5/1987 |
| EP | 0 627 206 | 12/1994 |

(Continued)

OTHER PUBLICATIONS

U.S. Appl. No. 11/899,004, Jan. 3, 2012 Issue Fee payment.
(Continued)

*Primary Examiner* — Long V Le
*Assistant Examiner* — Helene Bor
(74) *Attorney, Agent, or Firm* — Baker Botts L.L.P.

(57) ABSTRACT

Systems and methods for opening a tissue to a target value are disclosed herein. In an exemplary method, a region of the tissue is targeted for opening, a size range of microbubbles corresponding to the target value is determined, microbubbles of the size range are positioned in proximity to the targeted region, and an ultrasound beam is applied to the targeted region such that the tissue is opened with the assistance of the microbubbles to the target value.

50 Claims, 17 Drawing Sheets

(51) Int. Cl.
*A61B 19/00* (2006.01)
*A61B 8/08* (2006.01)

(56) References Cited

U.S. PATENT DOCUMENTS

| | | | |
|---|---|---|---|
| 4,822,679 A | 4/1989 | Cerdan-Diaz et al. | |
| 4,832,941 A | 5/1989 | Berwing et al. | |
| 4,858,613 A | 8/1989 | Fry et al. | |
| 4,926,675 A | 5/1990 | Schohl et al. | |
| 5,038,787 A | 8/1991 | Antich et al. | |
| 5,107,837 A | 4/1992 | Ophir et al. | |
| 5,178,147 A | 1/1993 | Ophir et al. | |
| 5,309,914 A | 5/1994 | Iinuma | |
| 5,433,708 A | 7/1995 | Nichols et al. | |
| 5,435,310 A | 7/1995 | Sheehan et al. | |
| 5,457,754 A | 10/1995 | Han et al. | |
| 5,601,084 A | 2/1997 | Sheehan et al. | |
| 5,606,971 A | 3/1997 | Sarvazyan | |
| 5,662,113 A | 9/1997 | Liu | |
| 5,722,411 A | 3/1998 | Suzuki et al. | |
| 5,741,522 A | 4/1998 | Violante et al. | |
| 5,752,515 A | 5/1998 | Jolesz et al. | |
| 5,810,731 A | 9/1998 | Sarvazyan et al. | |
| 5,840,028 A | 11/1998 | Chubachi et al. | |
| 5,928,151 A | 7/1999 | Hossack et al. | |
| 6,026,173 A | 2/2000 | Svenson et al. | |
| 6,028,066 A | 2/2000 | Unger | |
| 6,102,864 A | 8/2000 | Hatfield et al. | |
| 6,102,865 A | 8/2000 | Hossack et al. | |
| 6,106,465 A | 8/2000 | Napolitano et al. | |
| 6,123,669 A | 9/2000 | Kanda et al. | |
| 6,152,878 A | 11/2000 | Nachtomy et al. | |
| 6,193,951 B1 | 2/2001 | Ottoboni et al. | |
| 6,200,266 B1 | 3/2001 | Shokrollahi et al. | |
| 6,241,675 B1 | 6/2001 | Smith et al. | |
| 6,246,895 B1 | 6/2001 | Plewes | |
| 6,259,943 B1 | 7/2001 | Cosman et al. | |
| 6,309,355 B1 | 10/2001 | Cain et al. | |
| 6,312,382 B1 | 11/2001 | Mucci et al. | |
| 6,352,507 B1 | 3/2002 | Torp et al. | |
| 6,413,216 B1 | 7/2002 | Cain et al. | |
| 6,425,867 B1 | 7/2002 | Vaezy et al. | |
| 6,447,450 B1 | 9/2002 | Olstad | |
| 6,488,629 B1 | 12/2002 | Saetre et al. | |
| 6,491,636 B2 | 12/2002 | Chenal et al. | |
| 6,508,768 B1 | 1/2003 | Hall et al. | |
| 6,514,221 B2 * | 2/2003 | Hynynen et al. | 601/2 |
| 6,529,770 B1 | 3/2003 | Grimblatov | |
| 6,537,217 B1 | 3/2003 | Bjærum et al. | |
| 6,537,221 B2 | 3/2003 | Criton et al. | |
| 6,671,541 B2 | 12/2003 | Bishop et al. | |
| 6,683,454 B2 | 1/2004 | Rehwald et al. | |
| 6,685,641 B2 | 2/2004 | Liu et al. | |
| 6,689,060 B2 | 2/2004 | Phelps et al. | |
| 6,701,341 B1 | 3/2004 | Wu | |
| 6,770,033 B1 | 8/2004 | Fink et al. | |
| 6,875,176 B2 | 4/2005 | Mourad et al. | |
| 6,936,151 B1 | 8/2005 | Lock et al. | |
| 6,994,673 B2 | 2/2006 | Lysyansky et al. | |
| 7,016,719 B2 | 3/2006 | Rudy et al. | |
| 7,055,378 B2 | 6/2006 | Su et al. | |
| 7,136,518 B2 | 11/2006 | Griffin et al. | |
| 7,257,244 B2 | 8/2007 | Miga | |
| 7,331,926 B2 | 2/2008 | Varghese et al. | |
| 7,344,509 B2 | 3/2008 | Hynynen et al. | |
| 7,421,101 B2 | 9/2008 | Georgescu et al. | |
| 7,429,249 B1 | 9/2008 | Winder et al. | |
| 7,449,306 B2 | 11/2008 | Elson et al. | |
| 7,601,122 B2 | 10/2009 | Zagzebski et al. | |
| 7,753,847 B2 | 7/2010 | Greenleaf et al. | |
| 7,809,426 B2 | 10/2010 | Kim et al. | |
| 7,896,821 B1 * | 3/2011 | Magnin et al. | 601/2 |
| 8,029,444 B2 | 10/2011 | Pedrizzetti et al. | |
| 8,257,338 B2 * | 9/2012 | Keenan et al. | 604/500 |
| 2002/0034757 A1 | 3/2002 | Cubicciotti | |
| 2002/0038086 A1 | 3/2002 | Hynynen et al. | |
| 2002/0039594 A1 | 4/2002 | Unger | |
| 2002/0065461 A1 | 5/2002 | Cosman | |
| 2002/0095081 A1 | 7/2002 | Vilsmeier | |
| 2002/0151792 A1 | 10/2002 | Conston et al. | |
| 2002/0169394 A1 | 11/2002 | Eppstein et al. | |
| 2002/0193784 A1 | 12/2002 | McHale et al. | |
| 2003/0097068 A1 | 5/2003 | Hossack et al. | |
| 2003/0125621 A1 | 7/2003 | Drukker et al. | |
| 2003/0171672 A1 | 9/2003 | Varghese et al. | |
| 2003/0174890 A1 | 9/2003 | Yamauchi | |
| 2003/0220556 A1 | 11/2003 | Porat et al. | |
| 2004/0006266 A1 | 1/2004 | Ustuner et al. | |
| 2004/0049134 A1 | 3/2004 | Tosaya et al. | |
| 2004/0054357 A1 * | 3/2004 | O'Donnell | 606/4 |
| 2004/0059224 A1 | 3/2004 | Varghese et al. | |
| 2004/0092816 A1 | 5/2004 | Ossmann et al. | |
| 2004/0097805 A1 | 5/2004 | Verard et al. | |
| 2004/0172081 A1 | 9/2004 | Wang | |
| 2004/0210134 A1 | 10/2004 | Hynynen et al. | |
| 2004/0210135 A1 | 10/2004 | Hynynen | |
| 2004/0236219 A1 | 11/2004 | Liu et al. | |
| 2004/0249580 A1 | 12/2004 | Pourcelot et al. | |
| 2004/0258760 A1 | 12/2004 | Wheatley et al. | |
| 2005/0004466 A1 | 1/2005 | Hynynen et al. | |
| 2005/0054930 A1 | 3/2005 | Rickets et al. | |
| 2005/0059876 A1 | 3/2005 | Krishnan | |
| 2005/0080336 A1 | 4/2005 | Byrd et al. | |
| 2005/0080469 A1 | 4/2005 | Larson et al. | |
| 2005/0084538 A1 | 4/2005 | Dayton et al. | |
| 2005/0175541 A1 | 8/2005 | Lanza et al. | |
| 2005/0201942 A1 | 9/2005 | Dugstad et al. | |
| 2005/0203395 A1 | 9/2005 | Sui et al. | |
| 2005/0203399 A1 | 9/2005 | Vaezy et al. | |
| 2005/0259864 A1 | 11/2005 | Dickinson et al. | |
| 2005/0267695 A1 | 12/2005 | German | |
| 2005/0277824 A1 | 12/2005 | Aubry et al. | |
| 2005/0277835 A1 | 12/2005 | Angelsen et al. | |
| 2006/0034904 A1 | 2/2006 | Weimann | |
| 2006/0058651 A1 | 3/2006 | Chiao et al. | |
| 2006/0058671 A1 | 3/2006 | Vitek et al. | |
| 2006/0058673 A1 | 3/2006 | Aase et al. | |
| 2006/0074315 A1 | 4/2006 | Liang et al. | |
| 2006/0078501 A1 | 4/2006 | Goertz et al. | |
| 2006/0173320 A1 | 8/2006 | Radulescu | |
| 2006/0241529 A1 | 10/2006 | Hynynen et al. | |
| 2007/0049824 A1 | 3/2007 | Konofagou et al. | |
| 2007/0055179 A1 | 3/2007 | Deem et al. | |
| 2007/0059247 A1 * | 3/2007 | Lindner et al. | 424/9.52 |
| 2007/0129652 A1 | 6/2007 | Nita | |
| 2007/0207194 A1 | 9/2007 | Grayburn et al. | |
| 2007/0219447 A1 | 9/2007 | Kanai et al. | |
| 2007/0232962 A1 | 10/2007 | Zumeris et al. | |
| 2007/0239001 A1 | 10/2007 | Mehi et al. | |
| 2007/0276242 A1 | 11/2007 | Konofagou | |
| 2007/0276245 A1 | 11/2007 | Konofagou et al. | |
| 2008/0089848 A1 | 4/2008 | DiMauro | |
| 2008/0194957 A1 | 8/2008 | Hoctor et al. | |
| 2008/0200417 A1 | 8/2008 | Semple et al. | |
| 2008/0243214 A1 | 10/2008 | Koblish | |
| 2008/0260802 A1 | 10/2008 | Sawhney et al. | |
| 2008/0269606 A1 | 10/2008 | Matsumura | |
| 2008/0269668 A1 | 10/2008 | Keenan et al. | |
| 2008/0285819 A1 | 11/2008 | Konofagou et al. | |
| 2008/0319375 A1 | 12/2008 | Hardy | |
| 2009/0005711 A1 | 1/2009 | Konofagou et al. | |
| 2009/0191244 A1 | 7/2009 | Kheir et al. | |
| 2009/0221916 A1 | 9/2009 | Konofagou et al. | |
| 2009/0247911 A1 | 10/2009 | Novak et al. | |
| 2009/0270790 A1 | 10/2009 | Raghavan | |
| 2010/0286527 A1 | 11/2010 | Cannon et al. | |
| 2011/0028854 A1 | 2/2011 | Addison et al. | |
| 2011/0098562 A1 | 4/2011 | Salgo et al. | |
| 2011/0208038 A1 | 8/2011 | Konofagou et al. | |
| 2012/0004693 A1 | 1/2012 | Lo et al. | |
| 2013/0046229 A1 | 2/2013 | Konofagou et al. | |
| 2013/0066211 A1 | 3/2013 | Konofagou et al. | |
| 2013/0131495 A1 | 5/2013 | Konofagou et al. | |
| 2013/0204166 A1 | 8/2013 | Villanueva et al. | |

(56) References Cited

U.S. PATENT DOCUMENTS

| | | |
|---|---|---|
| 2013/0289398 A1 | 10/2013 | Borden et al. |
| 2013/0315491 A1 | 11/2013 | Konofagou et al. |
| 2014/0114216 A1 | 4/2014 | Konofagou et al. |
| 2015/0045724 A1 | 2/2015 | Chen et al. |
| 2015/0065871 A1 | 3/2015 | Konofagou et al. |

FOREIGN PATENT DOCUMENTS

| | | |
|---|---|---|
| WO | WO 99/37938 | 8/1999 |
| WO | WO 2005/030171 | 4/2005 |
| WO | WO 2007/148279 | 12/2007 |
| WO | WO 2008/015012 | 2/2008 |
| WO | WO2008/027520 | 3/2008 |
| WO | WO2008/062342 | 5/2008 |
| WO | WO 2008/131217 | 10/2008 |
| WO | WO2008/131302 | 10/2008 |
| WO | WO2008/157422 | 12/2008 |
| WO | WO2010/044385 | 4/2010 |
| WO | WO2010/063951 | 6/2010 |
| WO | WO 2011/028690 | 3/2011 |
| WO | WO2011/035312 | 3/2011 |

OTHER PUBLICATIONS

U.S. Appl. No. 11/433,510, Sep. 30, 2011 Final Office Action.
U.S. Appl. No. 11/433,510, May 23, 2011 Response to Non-Final Office Action.
U.S. Appl. No. 11/433,510, Jan. 21, 2011 Non-Final Office Action.
U.S. Appl. No. 11/433,510, Oct. 28, 2010 Response to Non-Final Office Action.
U.S. Appl. No. 11/433,510, Apr. 28, 2010 Non-Final Office Action.
U.S. Appl. No. 11/433,510, Apr. 13, 2010 Amendment and Request for Continued Examination (RCE).
U.S. Appl. No. 11/433,510, Nov. 12, 2009 Final Office Action.
U.S. Appl. No. 11/433,510, Aug. 6, 2009 Response to Non-Final Office Action.
U.S. Appl. No. 11/433,510, Mar. 17, 2009 Non-Final Office Action.
U.S. Appl. No. 11/697,573, Aug. 18, 2011 Amendment and Request for Continued Examination (RCE).
U.S. Appl. No. 11/697,573, Mar. 18, 2011 Final Office Action.
U.S. Appl. No. 11/697,573, Dec. 22, 2010 Response to Non-Final Office Action.
U.S. Appl. No. 11/697,573, Jun. 23, 2010 Non-Final Office Action.
U.S. Appl. No. 11/697,579, Apr. 29, 2011 Final Office Action.
U.S. Appl. No. 11/697,579, Feb. 7, 2011 Response to Non-Final Office Action.
U.S. Appl. No. 11/697,579, Aug. 6, 2010 Non-Final Office Action.
U.S. Appl. No. 11/697,579, May 17, 2010 Response to Non-Final Office Action.
U.S. Appl. No. 11/697,579, Nov. 17, 2009 Non-Final Office Action.
U.S. Appl. No. 11/697,579, Oct. 15, 2009 Amendment and Request for Continued Examination (RCE).
U.S. Appl. No. 11/697,579, Jul. 15, 2009 Response to Final Office Action.
U.S. Appl. No. 11/697,579, Apr. 15, 2009 Final Office Action.
U.S. Appl. No. 11/697,579, Jan. 16, 2009 Response to Non-Final Office Action.
U.S. Appl. No. 11/697,579, Jul. 18, 2008 Non-Final Office Action.
U.S. Appl. No. 12/077,612, Oct. 26, 2011 Amendment and Request for Continued Examination (RCE).
U.S. Appl. No. 12/077,612, May 26, 2011 Final Office Action.
U.S. Appl. No. 12/077,612, Mar. 23, 2011 Response to Non-Final Office Action.
U.S. Appl. No. 12/077,612, Nov. 16, 2010 Non-Final Office Action.
U.S. Appl. No. 12/096,254, Oct. 5, 2011 Non-Final Office Action.
U.S. Appl. No. 11/899,004, Oct. 4, 2011 Amendment after Notice of Allowance.
U.S. Appl. No. 11/899,004, Oct. 3, 2011 Notice of Allowance.
U.S. Appl. No. 11/899,004, Sep. 23, 2011 Amendment and Request for Continued Examination (RCE).
U.S. Appl. No. 11/899,004, Jul. 18, 2011 Notice of Allowance.
U.S. Appl. No. 11/899,004, May 10, 2011 Response to Non-Final Office Action.
U.S. Appl. No. 11/899,004, Feb. 8, 2011 Non-Final Office Action.
Abbott et al., "Astrocyte-Endothelial Interactions At the Blood-Brain Barrier," Nat. Rev. Neurosci., vol. 7, No. 1, pp. 41-53, 2006.
Ammi et al., "Ultrasonic contrast agent shell rupture detected by inertial cavitation and rebound signals", IEEE Transactions, 53(1): 126-136, Jan. 2006.
Ashikaga et al., "Transmural Dispersion of Myofiber Mechanics: Implications for Electrical Heterogeneity In Vivo," Journal of the American College of Cardiology, vol. 49, No. 8, 909-916, 2007.
Aubry et al., "Experimental Demonstration of Noninvasive Trans-skull Adaptive Focusing Based on Prior Computed Tomography Scans," The Journal of the Acoustical Society of America, vol. 113, p. 84, 2003.
Avolio, A. P., S. G. Chen, R. P. Wang, C. L. Zhang, M. F. Li and M. F. O'Rourke. "Effects of aging on changing arterial compliance and left ventricular load in a northern Chinese urban community", Circulation (1983) 68(1): 50-8.
Azuma et al., "Bubble Generation by Standing Wave in Water Surrounded by Cranium With Transcranial Ultrasonic Beam," Japanese Journal of Applied Physics, vol. 44, pp. 4625-4630, 2005.
Badke et al., "Effects of Ventricular Pacing on Regional Left Ventricular Performance in the Dog," Am J Physiol Heart Circ Physiol, vol. 238:H858-867, 1980.
Baron et al., "Simulation of Intracranial Acoustic Fields in Clinical Trials of Sonothrombolysis," Ultrasound Med. Biol., vol. 35, No. 7, pp. 1148-1158, 2009.
Baseri et al., "Multi-Modality Safety Assessment of Blood-Brain Barrier Opening Using Focused Ultrasound and Definity Microbubbles: A Short-Term Study," Ultrasound Med. Biol., vol. 6, No. 9, pp. 1445-1459, 2010.
Behrens et al., "Low-Frequency, Low-Intensity Ultrasound Accelerates Thrombolysis Through the Skull," Ultrasound in Medicine & Biology, vol. 25, pp. 269-273, 1999.
Bercoff, J., Tanter, M., and Fink, M, (2004). "Supersonic shear imaging: A new technique for soft tissue elasticity mapping." *IEEE Transactions on Ultrasonics Ferroelectrics and Frequency Control* 51, 396-409.
Berger et al., "Single-Beat Noninvasive Imaging of Cardiac Electrophysiology of Ventricular Pre-Excitation," Journal of the American College of Cardiology, vol. 48, pp. 2045-2052, 2006.
Bers, D.M., "Cardiac Excitation-Contraction Coupling," Nature, vol. 415, pp. 198-205, 2002.
Bonnefous, O. and P. Pesque. Time domain formulation of pulse-Doppler ultrasound and blood velocity estimation by cross correlation. Ultrason Imaging (1986) 8(2): 73-85.
Brekke et al., "Tissue doppler gated (TDOG) dynamic three-dimensional ultrasound imaging of the fetal heart", Ultrasound Obstet Gynecol, 2004, 24(2): 192-198.
Brooks, D. H., and MacLeod, R. S. (1997). Electrical imaging of the heart. *Ieee Signal Processing Magazine* 14, 24-42.
Brundin et al., "Restorative Therapies in Parkinsons Disease," Springer Verlag, 2006.
Campbell et al., "Mechanisms of Transmurally Varying Myocyte Electromechanics in an Integrated Computational Model," Philos Transact A Math Phys Eng Sci vol. 366, pp. 3361-3380, 2008.
Caskey et al., "Direct Observations of Ultrasound Microbubble Contrast Agent Interaction With the Microvessel Wall," J. Acoust. Soc. Amer., vol. 122, No. 2, pp. 1191-1200, 2007.
Caskey et al., "Microbubble Oscillation in Tubes With Diameters of 12, 25, and 195 Microns," Appl. Phys. Lett., vol. 88, No. 3, pp. 033902-1-033902-3, 2006.
Cavaglia et al., "Regional Variation in Brain Capillary Density and Vascular Response to Ischemia," Brain Res., vol. 910, No. 1-2, pp. 81-93, 2001.
Chan, A.W., "Transgenic Nonhuman Primates for Neurodegenerative Diseases," Reproductive Biology and Endocrinology, vol. 2, p. 39, 2004.
Chang et al. "3-D US Frame Positioning Using Speckle Decorrelation and Image Registration", Jun. 2003, Ultrasound in Medicine and Biology, pp. 801-812.

(56) References Cited

OTHER PUBLICATIONS

Chen et al., "Optimization of Ultrasound Parameters for Cardiac Gene Delivery of Adenoviral or Plasmid Deoxyribonucleic Acid by Ultrasound-Targeted Microbubble Destruction," J. Amer. Coll. Cardiol., vol. 42, No. 2, pp. 301-308, 2003.
Chen, Q. et al. "Estimation of Displacement Vectors and Strain Tensors in Elastography Using Angular Insonifications." *IEEE Transactions on Medical Imaging*, vol. 23, No. 12, pp. 1479-1489 (Dec. 1, 2004).
Choi et al., "Feasibility of Transcranial, Localized Drug-Delivery in the Brain of Alzheimers-Model Mice Using Focused Ultrasound," Ultrasonics Symposium, 2005 IEEE, Sep. 18-21, 2005, pp. 988-991.
Choi et al., "Molecules of Various Pharmacologically-Relevant Sizes Can Cross the Ultrasound-Induced Blood-Brain Barrier Opening In Vivo," Ultrasound in Medicine & Biology, 2009; 36(1): 58-67.
Choi et al., "Noninvasive, Transcranial and Localized Opening of the Blood-Brain Barrier Using Focused Ultrasound in Mice," Ultrasound in Medicine & Biology, 2007, 33(1): 95-104.
Choi et al., "Spatio-Temporal Analysis of Molecular Delivery Through the Blood-Brain Barrier Using Focused Ultrasound," Physics in Medicine and Biology, vol. 52, pp. 5509-5530, 2007.
Choi et al., "Focused Ultrasound-Induced Molecular Delivery Through the Blood-Brain Barrier," presented at the IEEE Symp. Ultrason. Ferroelect. Freq. Control, New York, NY, 2007:1192-1195.
Choi JJ, Wang S, Tung Y-S, Baseri B, Morrison B 3rd, Konofagou EE. "Delivery of pharmacologically-relevant sized molecules through the ultrasound-induced blood-brain barrier opening in vivo". Neuroscience, Chicago, IL, USA, Oct. 17-21. 2009.
Choi JJ, Wang S, Brown TR, Small SA, Duff KE and Konofagou EE, "Noninvasive and Transient Blood-Brain Barrier Opening in the Hippocampus of Alzheimer's Double Transgenic Mice Using Pulsed Focused Ultrasound", Ultrasonic Imaging 189-200, 2008.
Choi, J.J. et al., "Optimization of Blood-Brain Barrier Opening in Mice using Focused Ultrasound". 2006 IEEE Ultrasounics Symposium [online], Jun. 2007.
Choi et al., "Microbubble-size dependence of focused ultrasound-induced blood-brain barrier opening in mice in vivo" IEEE transactions on Biomedical engineering, Jan. 2010, 57(1): 145-154.
Chomas et al., "Threshold of Fragmentation for Ultrasonic Contrast Agents," J. Biomed. Opt., 2001, 6(2): 141-150.
Clement et al., "A Hemisphere Array for Non-Invasive Ultrasound Brain Therapy and Surgery," Phys Med Biol, vol. 45, pp. 3707-3719, Dec. 2000.
Connor et al., "A Unified Model for the Speed of Sound in Cranial Bone Based on Genetic Algorithm Optimization," Physics in Medicine and Biology, vol. 47, pp. 3925-3944, 2002.
Connor, C.W., "Simulation Methods and Tissue Property Models for Non-Invasive Transcranial Focused Ultrasound Surgery," Ph.D. Thesis, 2005.
Cordeiro et al., "Transmural Heterogeneity of Calcium Activity and Mechanical Function in the Canine Left Ventricle,"Am J Physiol Heart Circ Physiol, vol. 286, pp. H1471-H1479, 2004.
Coyle, P., "Spatial Features of the Rat Hippocampal Vascular System," Exp. Neurol., 58(3): 549-561, 1978.
Coyle, P., "Arterial Patterns of the Rat Rhinencephalon and Related Structures," Exp. Neurol., 49(3): 671-690, 1975.
Coyle, P., "Vascular Patterns of the Rat Hippocampal Formation," Exp. Neurol., 52(3): 447-458, 1976.
Crum, L.A., "Bjerknes Forces on Bubbles in a Stationary Sound Field," The Journal of the Acoustical Society of America, 57(6): 1363-1370, 1975.
Cutnell, J. and W. Kenneth (1998). Physics, Fourth Edition, New York. Table of Contents.
Daffertshofer et al., "Transcranial Low-Frequency Ultrasound-Mediated Thrombolysis in Brain Ischemia: Increased Risk of Hemorrhage With Combined Ultrasound and Tissue Plasminogen Activator: Results of a Phase II Clinical Trial," Stroke, vol. 36, p. 1441-1146, 2005.

Datta et al., "Correlation of Cavitation With Ultrasound Enhancement of Thrombolysis," Ultrasound in Medicine & Biology, 32(8): 1257-1267, 2006.
Declerck, J., T. S. Denney, C. Ozturk, W. O'Dell and E. R. McVeigh, "Left ventricular motion reconstruction from planar tagged MR images: a comparison." Phys Med Biol (2000) 45(6): 1611-1632.
Deffieux et al., "Transcranial Focused Ultrasound for Blood-Brain Barrier Opening—Numerical Simulations With In Vitro Validation in Human and Monkey Skulls," Title page and Table of Contents for the AIUM Annual Convention, San Diego, CA, 2010.
DeLong, M.R., "Primate Models of Movement Disorders of Basal Ganglia Origin," Trends Neurosci., 13(7): 281-285, 1990.
Duck, F., "Physical Properties of Tissue: A Comprehensive Reference Book," Academic Press, London, UK, 1990.
Durrer et al., "Total Excitation of the Isolated Human Heart," Circulation, vol. 41, pp. 899-912, 1970.
Edwards, C. H., Rankin, J. S., Mchale, P. A., Ling, D., and Anderson, R. W. (1981). "Effects of Ischemia on Left-Ventricular Regional Function in the Conscious Dog", *American Journal of Physiology* 240, H413-H420.
Erpelding et al., "Bubble-Based Acoustic Radiation Force Using Chirp Insonation to Reduce Standing Wave Effects," Ultrasound in Medicine & Biology, 33(2): 263-269, 2007.
Everbach et al., "Cavitational Mechanisms in Ultrasound-Accelerated Thrombolysis At 1 Mhz," Ultrasound in Medicine & Biology, 26(7): 1153-1160, 2000.
Faris et al., "Novel Technique for Cardiac Electromechanical Mapping With Magnetic Resonance Imaging Tagging and an Epicardial Electrode Sock," Ann Biomed Eng. vol. 31, pp. 430-440, 2003.
Farook et al., "Preparation of Microbubble Suspensions by Co-Axial Electrohydrodynamic Atomization," Med. Eng. Phys., 29(7): 749-754, 2007.
Fiske et al., "Special Focus Section: Gene Therapy for Parkinsons Disease," Experimental Neurology, vol. 209, pp. 28-29, 2008.
Fry et al., "A Focused Ultrasound System for Tissue Volume Ablation in Deep Seated Brain Sites," IEEE 1986 Ultrasonics Symposium, pp. 1001-1004, 1986.
Fry, F.J., "Transkull Transmission of an Intense Focused Ultrasonic Beam," Ultrasound in Medicine & Biology, vol. 3, p. 179, 1977.
Fung, Y. C. (1993). Biomechanics—Mechanical Properties of Living Tissues. New York. Table of Contents.
Ganan-Calvo et al., "Perfectly Monodisperse Microbubbling by Capillary Flow Focusing," Phys. Rev. Lett., 87(27) Pt 1: 274501-1-274501-4, 2001.
Gaud et al., "Acoustic characterization of single ultrasound contrast agent microbubbles", The Journal of the Acoustic Society of America, 124(6): 4091, 2008.
Ghosh et al., "Cardiac Memory in Patients With Wolff-Parkinson-White Syndrome: Noninvasive Imaging of Activation and Repolarization Before and After Catheter Ablation," Circulation, vol. 118, pp. 907-915, 2008.
Giacobini, E., "Alzheimer Disease, From Molecular Biology to Therapy," Advances in Experimental Medicine and Biology, vol. 429, p. 235-245, 1997.
Greenstein et al., "Mechanisms of Excitation-Contraction Coupling in an Integrative Model of the Cardiac Ventricular Myocyte," Biophysical Journal, vol. 90 pp. 77-91, 2006.
Greenwald, S. E., "Pulse pressure and arterial elasticity.", Qjm-an International Journal of Medicine (2002) 95(2): 107-112.
Gupta, K. B., Ratcliffe, M. B., Fallert, M. A., Edmunds, L. H., and Bogen, D. K. (1994). Changes in Passive Mechanical Stiffness of Myocardial Tissue with Aneurysm Formation. *Circulation* 89, 2315-2326.
Gurev et al., "Distribution of Electromechanical Delay in the Heart: Insights From a Three-Dimensional Electromechanical Model," Biophysical Journal, vol. 99 pp. 745-754, 2010.
Gurev et al., "In Silico Characterization of Ventricular Activation Pattern by Electromechanical Wave Imaging," Supplement to Heart Rhythm, vol. 6, p. S357, 2009.
Heimdal, A., A. Stoylen, H. Torp and T. Skjaerpe. Real-time strain rate imaging of the left ventricle by ultrasound. J Am Sac Echocardiog (1998) 11(11): 1013-1019.

(56) References Cited

OTHER PUBLICATIONS

Henderson, A., Parmley, W. W., and Sonnenbl, E. (1971). Series Elasticity of Heart Muscle During Hypoxia. *Cardiovascular Research* 5, 10-14.
Huang et al. "Watershed Segmentation for Breast Tumor in 2-D Sonography", May 2004, Ultrasound in Medicine and Biology, pp. 625-632.
Hynynen et al., "Demonstration of Potential Noninvasive Ultrasound Brain Therapy Through an Intact Skull," Ultrasound in Medicine & Biology, 24(2): 275-283, 1998.
Hynynen et al., "Noninvasive MR Imaging—Guided Focal Opening of the Blood-Brain Barrier in Rabbits," Radiology, 220(3): 640-646, 2001.
Hynynen et al., "Trans-Skull Ultrasound Therapy: The Feasibility of Using Image-Derived Skull Thickness Information to Correct the Phasedistortion," IEEE Transactions on Ultrasonics, Ferroelectrics and Frequency Control, 46(3): 752-755, 1999.
Hynynen, N. et al., "Focal Disruption of the Blood-Brain Barrier Due to 260-Khz Ultrasound Bursts: A Method for Molecular Imaging and Targeted Drug Delivery," J. Neurosurg., 105(3): 445-454, 2006.
International Search Report for PCT/US07/19149 dated Feb. 29, 2008.
International Search Report for PCT/US06/061809 dated Oct. 4, 2007.
International Search Report for PCT/US06/18454 dated Aug. 9, 2007.
International Search Report for PCT/US05/37669 dated Jun. 13, 2006.
International Search Report for PCT/US05/37670 dated Nov. 22, 2006.
International Search Report and Written Opinion of the International Searching Authority for PCT/US09/052563 dated Oct. 8, 2009.
EPO Search Report & Opinion and Office Action for EP0684017.2 dated Dec. 7, 2009.
International Search Report and Written Opinion of the International Searching Authority for PCT/US09/056565 dated Nov. 2, 2009.
International Search Report and Written Opinion for PCT/US06/36460, dated Sep. 5, 2007; International Preliminary Report dated Mar. 26, 2008.
J.A. Feshitan et al., Microbubble size isolation by differential centrifugation, Journal of Colloid and Interface Science 329 (2009) 316-324.
Jagannathan et al., "High-Intensity Focused Ultrasound Surgery of the Brain: Part 1-A Historical Perspective With Modern Applications," Neurosurgery, 64(2): 201-211, 2009.
Jensen et al., "Calculation of Pressure Fields From Arbitrarily Shaped, Apodized, and Excited Ultrasound Transducers," IEEE Transactions on Ultrasonics, Ferroelectrics and Frequency Control, 39(2):262-267, 1992.
Kallel et al., "A Least-Squares Strain Estimator for Elastography," Ultrason Imaging, vol. 19, pp. 195-208, 1997.
Kanai, H., "Propagation of spontaneously actuated pulsive vibration in human heart wall and in vivo viscoelasticity estimation." Ieee T Ultrason Ferr (2005) 52(11): 1931-1942.
Kanai, H. and Y. Koiwa, "Myocardial rapid velocity distribution." Ultrasound Med Biol (2001) 27(4): 481-498.
Kanai, H., A. Umezawa and Y. Koiwa, (2000) "Transcutaneous measurement of frequency dispersion in the regional pulse wave velocity." IEEE Ultrasonics symposium.
Kanai, H., H. Satoh, K. Hirose and N. Chubachi. A New Method for Measuring Small Local Vibrations in the Heart Using Ultrasound. Ieee T Bio-Med Eng (1993) 40(12): 1233-1242.
Kaufman et al., "Ultrasound Simulation in Bone," IEEE Transactions on Ultrasonics Ferroelectrics and Frequency Control, 55(6): 1205-1218, 2008.
Kimber et al., "A Comparison of Unipolar and Bipolar Electrodes During Cardiac Mapping Studies," Pacing Clin Electro, vol. 19, pp. 1196-1204, 1996.
Kinoshita et al., "Noninvasive Localized Delivery of Herceptin to the Mouse Brain by MRI-Guided Focused Ultrasound-Induced Blood-Brain Barrier Disruption," Proceedings of the National Academy of Sciences, 103(31): 11719-11723, 2006.
Kinoshita et al., "Targeted Delivery of Antibodies Through the Blood-Brain Barrier by MRI-Guided Focused Ultrasound," Biochemical and Biophysical Research Communications, vol. 340, pp. 1085-1090, 2006.
Klein et al., "Interdependency of Local Capillary Density, Blood Flow, and Metabolism in Rat Brains," Amer. J. Physiol., 251(6) Pt 2: H1333-H1340, 1986.
Klempner et al., "Neutrophil Plasma Membranes I. High-Yield Purification of Human Neutrophil Plasma Membrane Vesicles by Nitrogen Cavitation and Differential Centrifugation," Journal of Cell Biology, vol. 86, pp. 21-28, 1980.
Konofagou et al., "Mechanism and Safety At the Threshold of the Blood-Brain Barrier Opening In Vivo," International Society on Therapeutic Ultrasound (ISTU), Aix-en-Provence, France, Sep. 21-24, 2009.
Konofagou et al., "Noninvasive Electromechanical Wave Imaging and Conduction Velocity Estimation In Vivo," Ultrasonics Symposium, 2007 IEEE, pp. 969-972, 2007.
Konofagou E.E. and Ophir, J., (1998) "A New Elastographic Method for Estimation and Imaging of Lateral Strains, Corrected Axial Strains and Poison's Ratios in Tissues", Ultrasound in Medicine and Biology 24(8), 1183-1199.
Konofagou E.E., Kallel F. and Ophir J., (1998) "Three-dimensional Motion estimation in Elastography", IEEE Proceedings of the Symposium of Ultrasonics, Ferroelectrics and Frequency Control in Sendai, Japan, 1745-1748.
Konofagou E.E., D'Hooge J.D., Ophir, J Myocardial Elastography—Feasibility Study In Vivo. *Ultrasound Med & Biol.*, vol. 28, No. 4, pp. 475-482 (2002).
Konofagou E E et al. "Elastographic Imaging of the Strain Distribution at the Anterior Cruciate Ligament and ACL-Bone Insertions" *27th Annual International Conference of the Engineering in Medicine and Biology Society*, pp. 972-975 (Shanghai, China Sep. 1-4, 2005).
Konofagou et al., "noninvasive Electromechanical Wave Imaging and Conduction Velocity Estimation In Vivo", Ultrasonics Symposium, 2007 IEEE, pp. 969-972, 2007.
Korecka et al., "Cell-Replacement and Gene-Therapy Strategies for Parkinsons and Alzheimers Disease," Regen. Med., 2(4): 425-446, 2007.
Kremkau et al., "Ultrasonic Attenuation and Propagation Speed in Normal Human Brain," The Journal of the AcouStical Society of America, vol. 70, p. 29, 1981.
Kunz et al., "The Finite Difference Time Domain Method for Electromagnetics," CRC Press, Boca Raton, USA, 1993.
Kvale et al., "Size Fractionation of Gas-Filled Microspheres by Flotation," Separations Technol., 6(4): 219-226, 1996.
Lai et al., "Introduction to Continuum Mechanics," (Pergamon Pr). 3rd Ed., 1993.
Lee et al., "Improving Stereotactic Surgery Using 3-D Reconstruction," IEEE Engineering in Medicine and Biology Magazine, vol. 21, pp. 109-116, 2002.
Lee et al., "Theoretical Quality Assessment of Myocardial Elastography With in Vivo Validation," Ultrasonics, Ferroelectrics and Frequency Control, IEEE Transactions on vol. 54, pp. 2233-2245, 2007.
Liu et al., "Hemorrhage Detection During Focused-Ultrasound Induced Blood-Brain-Barrier Opening by Using Susceptibility-Weighted Magnetic Resonance Imaging," Ultrasound in Med. & Biol., 34(4): 598-606, 2008.
Liu et al., "Magnetic Resonance Imaging Enhanced by Superparamagnetic Iron Oxide Particles: Usefulness for Distinguishing Between Focused Ultrasound-Induced Blood-Brain Barrier Disruption and Brain Hemorrhage," J. of Magnetic Resonance Imaging, vol. 29, pp. 31-38, 2009.
Lu et al., "Design and Experiment of 256-Element Ultrasound Phased Array for Noninvasive Focused Ultrasound Surgery," Ultrasonics, vol. 44, pp. 325-330, 2006.
Luo et al., "A Fast Normalized Cross-Correlation Method for Motion Estimation," IEEE Trans. Ultrason. Ferroelectr. Control, 57(6): 1347-1357, 2010.

(56) References Cited

OTHER PUBLICATIONS

Luo et al., "High-Frame Rate, Full-View Myocardial Elastography With Automated Contour Tracking in Murine Left Ventricles In Vivo," Ultrasonics, Ferroelectrics and Frequency Control, IEEE Transactions, 55(1): 240-248, 2008.
Luo et al., "Myocardial Elastography At Both High Temporal and Spatial Resolution for the Detection of Infarcts," Ultrasound Med. Biol., 33(8): 1206-1223, 2007.
Luo et al., "Pulse Wave Imaging of Normal and Aneurysmal Abdominal Aortas in Vivo," IEEE Trans. Med. Imaging, 28(4): 477-486, 2009.
Maleke et al., "In Vivo Feasibility of Real-Time Monitoring of Focused Ultrasound Surgery (FUS) Using Harmonic Motion Imaging (HMI)," IEEE Trans. Biomed. Eng., 57(1): 7-11, Jan. 2010.
Maleke et al., "Single-Element Ultrasound Focused Ultrasound Transducer Method for Harmonic Motion Imaging," Ultrasonic Imaging, 28(3): 144-158, 2006.
Marquet et al., "Non-Invasive Transcranial Ultrasound Therapy Based on a 3D CT Scan: Protocol Validation and In Vitro Results," Phys. Med. Biol, vol. 54, pp. 2597-2613, 2009.
Mazziotta et al., "A Probabilistic Atlas of the Human Brain: Theory and Rationale for Its Development the International Consortium for Brain Mapping (ICBM)," Neuroimage, vol. 2, pp. 89-101, 1995.
McDannold et al., "Targeted Disruption of the Blood-Brain Barrier With Focused Ultrasound: Association With Cavitation Activity," Physics in Medicine and Biology, vol. 51, pp. 793-808, 2006.
McDannold et al., "Use of Ultrasound Pulses Combined With Definity for Targeted Blood-Brain Barrier Disruption: A Feasibility Study," Ultrasound in Medicine & Biology, 33(4): 584-590, 2007.
McDannold et al., "MRI-Guided Targeted Blood-Brain Barrier Disruption With Focused Ultrasound: Histological Findings in Rabbits," Ultrasound Med. Biol., 31(11): 1527-1537, 2005.
McDannold, N. et al., Blood-Brain Barrier Disruption Induced by Focused Ultrasound and Circulating Preformed Microbubbles Appears to be Characterized by the Mechnical Index. Ultrasound Med Biol. Jan. 2008, v. 34(5), pp. 834-840.
McLaughlin, J., M. McNeill, B. Braun and P. D. McCormack, "Piezoelectric sensor determination of arterial pulse wave velocity." Physiol Meas (2003) 24(3): 693-702.
McNally, D. et al. "Computer Vision Elastography: Speckle Adaptive Motion Estimation for Elastography Using Ultrasound Sequences." *IEEE Transactions on Medical Imaging*, vol. 24, No. 6, pp. 755-766 (2005).
Melodelima et al., "Thermal Ablation by High-Intensity-Focused Ultrasound Using a Toroid Transducer Increases the Coagulated Volume. Results of Animal Experiments," Ultrasound in Medicine & Biology, 35(3): 425-435, 2009.
Mitri et al., "Chirp Imaging Vibro-Acoustography for Removing the Ultrasound Standing Wave Artifact," IEEE transactions on medical imaging, 24(10): 1249-1255, 2005.
Mychaskiw et al., "Optison (FS069) Disrupts the Blood-Brain Barrier in Rats," Anesthesia & Analgesia, vol. 91, p. 798, 2000.
Nichols, W. and M. F. O'Rourke (1998). Vascular impedance.In McDonald's: blood flow in arteries: theoretical, experimental and clinical principles. E. Arnold. London. Table of Contents.
Ophir et al., "Elastography: A Quantitative Method for Imaging the Elasticity of Biological Tissues," Ultrasonic Imaging, 3(2): 111-134, 1991.
Pardridge, W.M., "Drug Targeting to the Brain," Pharmaceutical research, vol. 24, pp. 1733-1744, 2007.
Pardridge, W.M., "The Blood-Brain Barrier: Bottleneck in Brain Drug Development," NeuroRx, vol. 2, pp. 3-14, 2005.
Patel et al., "GDNF Delivery for Parkinsons Disease," ACTA Neurochirurgica-supplementum, 97(2): 135-154, 2007.
Pernot et al., "ECG-Gated, Mechanical and Electromechanical Wave Imaging of Cardiovascular Tissues In Vivo," Ultrasound in Medicine & Biology, 33(7): 1075-1085, 2007.
Pernot et al., "Electromechanical Imaging of the Myocardium At Normal and Pathological States," Ultrasonics Symposium, 2005 IEEE, pp. 1091-1094, 2005.
Philippens, I.H., "Non-Human Primate Models for Parkinsons Disease," Drug Discovery Today: Disease Models, vol. 5, pp. 105-111, 2008.
Pichardo et al., "Multi Frequency Characterization of Speed of Sound for Longitudinal Transmission on Freshly Excised Human Skulls," in 9th International Society on Therapeutic Ultrasound, p. 136, 2009.
Prinzen et al., "The Time Sequence of Electrical and Mechanical Activation During Spontaneous Beating and Ectopic Stimulation," Eur. Heart J., vol. 13, pp. 535-543, 1992.
Provost et al., "Electromechanical Wave Imaging of Normal and Ischemic Hearts In Vivo," IEEE Trans. Med. Imaging, vol. 29, pp. 625-635, 2010.
Qin, S. and Ferrara, K.W., Acoustic response of compliable microvessels containing ultrasound contrast agents, Phys. Med. Biol. 51 (2006) 5065-5088.
Qin, S. and Ferrara, K.W., The Natural Frequency of Nonliner Oscillation of Ultrasound Contrast Agents in Microvessels, Ultrasound in Med. & Biol., vol. 33, No. 7, pp. 1140-1148, 2007.
Ramanathan et al., "Activation and Repolarization of the Normal Human Heart Under Complete Physiological Conditions," Proceedings of the National Academy of Sciences, vol. 103, pp. 6309-6314, 2006.
Ramanathan et al., "Noninvasive Electrocardiographic Imaging for Cardiac Electrophysiology and Arrhythmia," Nat Med, vol. 10, pp. 422-428, 2004.
Raymond et al., "Ultrasound Enhanced Delivery of Molecular Imaging and Therapeutic Agents in Alzheimers Disease Mouse Models," PLoS One, vol. 3, 2008.
Rice et al., "Approximate Model of Cooperative Activation and Crossbridge Cycling in Cardiac Muscle Using Ordinary Differential Equations," Biophys. J., vol. 95, pp. 2368-2390, 2008.
Rockenstein et al., "Transgenic Animal Models of Neurodegenerative Diseases and Their Application to Treatment Development," Adv. Drug Del. Rev., vol. 59, No. 11, pp. 1093-1102, 2007.
Rogers, W. J., Y. L. Hu, D. Coast, D. A. Vido, C. M. Kramer, R. E. Pyeritz and N. Reichek, "Age-associated changes in regional aortic pulse wave velocity." J Am Coll Cardiol (2001) 38(4): 1123-9.
Roth, B. J. (2000). Influence of a perfusing bath on the foot of the cardiac action potential. *Circulation Research* 86, E19-E22.
Sabraoui et al., "Feedback loop process to control acoustic cavitation" Ultrasonics Sonochemistry 18(2): 589-594, Mar. 2011.
Samuel et al., "An Ex Vivo Study of the Correlation Between Acoustic Emission and Microvascular Damage," Ultrasound Med. Biol., vol. 35, No. 9, pp. 1574-1586, 2009.
Sanberg et al., "Brief Communication: Neural Transplants Disrupt the Blood-Brain Barrier and Allow Peripherally Acting Drugs to Exert a Centrally Mediated Behavioral Effect," Experimental Neurology, vol. 102, pp. 149-152, 1988.
Sandrin, L., S. Catheline, M. Tanter, X. Hennequin and M. Fink. Time-resolved pulsed elastography with ultrafast ultrasonic imaging. Ultrason Imaging (1999) 21(4): 259-72.
Sarvazyan, A. P., O. V. Rudenko, S. D. Swanson, J. B. Fowlkes and S. Y. Emelianov. Shear wave elasticity imaging: A new ultrasonic technology of medical diagnostics. Ultrasound Med Biol (1998) 24(9): 1419-1435.
Sassaroli, E. and Hynynen, K., Forced linear oscillations of microbubbles in blood capillaries, J. Acoust. Soc. Am. 115 (6), Jun. 2004.
Sassaroli, E. and Hynynen, K., Resonance frequency of microbubbles in small blood vessels: a numerical study, Phys. Med. Biol. 50 (2005) 5293-5305.
Sassaroli, E. and Hynynen, K., Cavitation Threshold of Microbubbles in Gel Tunnels by Focused Ultrasound, Ultrasound in Med. & Biol., vol. 33, No. 10, pp. 1651-1660, 2007.
Schenk et al., "Immunization With Amyloid-Beta Attenuates Alzheimer-Disease-Like Pathology in the PDAPP Mouse," Nature, vol. 400, pp. 173-177, 1999.
Scher et al., "The Pathway of Ventricular Depolarization in the Dog," Circ Res, vol. 4, pp. 461-469, 1956.
Schilling et al., "Simultaneous Endocardial Mapping in the Human Left Ventricle Using a Noncontact Catheter: Comparison of Contact and Reconstructed Electrograms During Sinus Rhythm," Circulation, vol. 98, pp. 887-898, 1998.

(56) References Cited

OTHER PUBLICATIONS

Sengupta et al., "Electromechanical Activation Sequence in Normal Heart," Heart Fail Clin., vol. 4, pp. 303-314, 2008.
Shehata et al., "Myocardial Tissue Tagging With Cardiovascular Magnetic Resonance," Journal of Cardiovascular Magnetic Resonance, vol. 11, p. 55, 2009.
Sheikov et al., "Brain Arterioles Show More Active Vesicular Transport of Blood-Borne Tracer Molecules Than Capillaries and Venules After Focused Ultrasound-Evoked Opening of the Blood-Brain Barrier," Ultrasound Med. Biol., 32(9): 1399-1409, 2006.
Sheikov et al., "Cellular Mechanisms of the Blood-Brain Barrier Opening Induced by Ultrasound in Presence of Microbubbles," Ultrasound Med. Biol., 30(7): 979-989, 2004.
Sheikov et al., "Effect of Focused Ultrasound Applied With an Ultrasound Contrast Agent on the Tight Junctional Integrity of the Brain Microvascular Endothelium," Ultrasound Med. Biol., 34(7): 1093-1104, 2008.
Silva, G.A. Nanotechnology approaches to crossing the blood-brain barrier and drug delivery to the CNS, BMC Neruosci. 9(Suppl 3): S4, 2008.
Siegel et al., "Neurotrophic Factors in Alzheimers and Parkinsons Disease Brain," Brain Research Reviews, vol. 33, pp. 199-227, 2000.
Sinkus, R., J. Lorenzen, D. Schrader, M. Lorenzen, M. Dargatz and D. Holz, "High-resolution tensor MR elastography for breast tumour detection." Phys Med Biol (2000) 45(6): 1649-1664.
Sirsi et al., "Effect of Microbubble Size on Fundamental Mode High Frequency Ultrasound Imaging in Mice," Ultrasound in Med. & Bio., 36(6):935-948, 2010.
Spach, M. S., Heidlage, J. F., Dolber, P. C., and Barr, R. C. (1998). Extracellular discontinuities in cardiac muscle—Evidence for capillary effects on the action potential foot. *Circulation Research* 83, 1144-1164.
Stewart et al., "Blood-Eye Barriers in the Rat: Correlation of Ultrastructure With Function," J. Comp. Neurol., 340(4): 566-576, 1994.
Stieger et al., "Enhancement of Vascular Permeability With Low-Frequency Contrast-Enhanced Ultrasound in the Chorioallantoic Membrane Model," Radiology, 243(1): 112-121, 2007.
Styner et al., "Automatic Brain Segmentation in Rhesus Monkeys," Medical imaging, 2007.
Sutherland, G. R. Color Doppler Myocardial Imaging—Potential Applications in Acquired and Congenital Heart-Disease. Acta Paediatr (1995) 84: 40-48.
Sykova et al., "Diffusion in Brain Extracellular Space," Physiol. Rev., 88(4): 1277-1340, 2008.
Talu et al., "Tailoring the Size Distribution of Ultrasound Contrast Agents: Possible Method for Improving Sensitivity in Molecular Imaging," Mol. Imag., 6(6): 384-392, 2007.
Tang et al., "Standing-Wave Suppression for Transcranial Ultrasound by Random Modulation," IEEE transactions on Biomedical Engineering, vol. 57, issue 1, p. 203-205, 2010.
Tanter, M., J. Bercoff, L. Sandrin and M. Fink, "Ultrafast compound imaging for 2-D motion vector estimation: application to transient elastography." IEEE Trans Ultrason Ferroelectr Freq Control (2002) 49(10): 1363-74.
Tanter et al., "Focusing and Steering Through Absorbing and Aberrating Layers: Application to Ultrasonic Propagation Through the Skull," The Journal of the Acoustical Society of America, vol. 103, p. 2403, 1998.
Tavarozzi et al., "Magnetocardiography: Current Status and Perspectives Part II: Clinical Applications," Ital Heart J., vol. 3, pp. 151-165, 2002.
Treat et al., "Targeted Delivery of Doxorubicin to the Rat Brain At Therapeutic Levels Using MRI-Guided Focused Ultrasound," Int. J. Cancer, 121(4): 901-907, 2007.
Tung et al., "Identifying the Inertial Cavitation Threshold and Skull Effects in a Vessel Phantom Using Focused Ultrasound and Microbubbles," Ultrasound in Medicine & Biology, 36(5): 840-852, 2010.

Tung et al., "Identifying the Inertial Cavitation Threshold in a Vessel Phantom Using Focused Ultrasound and Microbubbles.," The Journal of the Acoustical Society of America, vol. 124, p. 2486, 2008.
Tung et al., "Feasibility of noninvasive cavitation-guided blood-brain barrier opening using focused ultrasound and microbubbles in non-human primates", Applied Physics Letters 98, No. 16, 2001, 163704.
Tung et al., "Noninvasive in vivo cavitation threshold detection during blood-brain barrier opening using focused ultrasound and the contrast agent and definity", Joint 159th Meeting of the Acoustic Society of America, Apr. 19, 2010.
Tuszynski et al., "A Phase 1 Clinical Trial of Nerve Growth Factor Gene Therapy for Alzheimer Disease," Nature medicine, vol. 11, p. 551, 2005.
Tuszynski et al., "Nerve Growth Factor Gene Therapy in Alzheimer Disease," Alzheimer Disease & Associated Disorders, vol. 21, p. 179, 2007.
Unger, E.C. et al., Therapeutic Applications of Lipid-Coated Microbubbles. Advanced Drug Delivery Reviews. May 2004, vol. 56(9), pp. 1291-1314.
Vappou et al., "Quantitative Viscoelastic Parameters Measured by Harmonic Motion Imaging," Phys. Med. Biol., vol. 54, pp. 3579-3595, 2009.
Walker et al., "A Fundamental Limit on the Performance of Correlation Based Phase Correction and Flow Estimation Techniques," Ultrasonics, Ferroelectrics and Frequency Control, IEEE Transactions, 41(5): 644-654, 1994.
Walker, W. F. and G. E. Trahey. A Fundamental Limit on Delay Estimation Using Partially Correlated Speckle Signals. Ieee T Ultrason Ferr (1995) 42(2): 301-308.
Wang et al., "A composite imaging technique for high frame-rate and full-view cardiovascular ultrasound and elasticity imaging"IEEE Transactions on Ultrasonics, Ferroelectrics and Frequency Control, 2008, 55(10): 2221-2233.
Wang et al., "A composite imaging technique for high frame-rate and full-view cardiovascular ultrasound and elasticity imaging",IEEE International Ultrasonics Symposium, New York, NY, Oct. 28-31, 2007.
Wang et al., "Qualitative and Quantitative Analysis of the Molecular Delivery Through the Ultrasound-Enhanced Blood-Brain Barrier Opening in the Murine Brain," presented at the IEEE Symp. Ultrason. Ferroelectr. Freq. Control, Beijing, China, 2008.
Wang, Y. X., M. Halks-Miller, R. Vergona, M. E. Sullivan, R. Fitch, C. Mallari, B. Martin-McNulty, V. da Cunha, A. Freay, G. M. Rubanyi and K. Kauser. Increased aortic stiffness assessed by pulse wave velocity in apolipoprotein E-deficient mice. Am J Physiol Heart Circ Physiol (2000) 278(2): H428-34.
Wenk, G.L., "A Primate Model of Alzheimers Disease," Behavioural Brain Research, vol. 57, pp. 117-122, 1993.
White et al., "Longitudinal and Shear Mode Ultrasound Propagation in Human Skull Bone," Ultrasound in Medicine & Biology, vol. 32, pp. 1085-1096, 2006.
Wyman et al., "Mapping Propagation of Mechanical Activation in the Paced Heart With MRI Tagging," Am J Physiol Heart Circ Physiol, vol. 276, pp. H881-H891, 1999.
Xu et al., "Controllable Gas-Liquid Phase Flow Patterns and Monodisperse Microbubbles in a Microfluidic T-Junction Device," Appl. Phys. Lett., 88(13): 133506-1-133506-3, 2006.
Yin et al., "A Numerical Study of Transcranial Focused Ultrasound Beam Propagation At Low Frequency," Physics in Medicine and Biology, vol. 50, pp. 1821-1836, 2005.
Yuh, EL, et. al. Delivery of Systemic Chemotherapeutic Agent to Tumors by Using Focused Ultrasound: Study in a Murine Model. Radiology, 234(2): 431-437, 2005.
Zerhouni, E. A., D. M. Parish, W. J. Rogers, A. Yang and E. P. Shapiro. Human heart: tagging with MR imaging—a method for noninvasive assessment of myocardial motion. Radiology (1988) 169(1): 59-63.
Zhang, et al., "Noninvasive Three-Dimensional Electrocardiographic Imaging of Ventricular Activation Sequence," Am J Physiol Heart Circ Physiol., vol. 289, pp. H2724-H2732, 2005.
Zheng et al., "Ultrasound-Driven Microbubble Oscillation and Translation Within Small Phantom Vessels," Ultrasound Med. Biol., 33(12): 1978-1987, 2007.

(56) References Cited

OTHER PUBLICATIONS

Zheng, Y.P. et al. "High Resolution ultrasound elastomicroscopy imaging of soft tissues: system development and feasibility; Ultrasound elastomicroscopy." *Physics in Medicine and Biology*, vol. 49, No. 17, pp. 3925-3938 (Sep. 7, 2004).
Zlokovic, V., "The Blood-Brain Barrier in Health and Chronic Neurodegenerative Disorders," Neuron, 57(2): 178-201, 2008.
Zwanenburg et al., "Timing of Cardiac Contraction in Humans Mapped by High-Temporal-Resolution MRI Tagging: Early Onset and Late Peak of Shortening in Lateral Wall," Am J Physiol Heart Circ Physiol., vol. 286, pp. H1872-H1880, 2004.
U.S. Appl. No. 13/353,148, filed Jan. 18, 2012.
U.S. Appl. No. 13/426,400, filed Mar. 21, 2012.
U.S. Appl. No. 13/529,239, filed Jun. 21, 2012.
U.S. Appl. No. 11/697,573, Jan. 18, 2013 Amendment and Request for Continued Examination (RCE).
U.S. Appl. No. 11/697,573, Jul. 18, 2012 Final Office Action.
U.S. Appl. No. 11/697,573, Jun. 27, 2012 Response to Non-Final Office Action.
U.S. Appl. No. 11/697,573, Jan. 26, 2012 Non-Final Office Action.
U.S. Appl. No. 11/433,510, Mar. 30, 2012 Amendment and Request for Continued Examination (RCE).
U.S. Appl. No. 11/433,510, Mar. 28, 2012 Advisory Action.
U.S. Appl. No. 11/433,510, Dec. 29, 2011 Response to Final Office Action.
U.S. Appl. No. 13/019,029, Dec. 26, 2012 Notice of Allowance.
U.S. Appl. No. 12/096,254, Nov. 30, 2012 Amendment and Request for Continued Examination (RCE).
Konofagou et al., "Electromechanical Wave Imaging for Noninvasive Mapping of the 3D Electrical Activation Sequence in Canines and Humans In Vivo", Journal of Biomechanics, 45(5):856-864 (2012).
Ohtani, et al., "Transmural Ultrasound-Based Visualization of Patterns of Action Potential Wave Propagation in Cardiac Tissue", Annals Biomedical Engineering, 38(10):3112-3123 (2010).
International Search Report and Written Opinion for PCT/US2010/049681, dated Dec. 7, 2010.
International Search Report and Written Opinion for PCT/US2010/061742, dated Mar. 1, 2011.
International Search Report and Written Opinion for PCT/US2009/056513, dated Oct. 30, 2009.
U.S. Appl. No. 12/077,612, Sep. 22, 2014 Amendment and Request for Continued Examination (RCE).
U.S. Appl. No. 12/096,254, Sep. 22, 2014 Amendment and Request for Continued Examination (RCE).
European Search Report for EP Application No. 10838238, dated May 6, 2014.
International Search Report and Written Opinion for PCT/US2011/034704, dated Aug. 18, 2011.
Borden et al., "Ultrasound Radiation Force Modulates Ligand Availability on Target Contrast Agents", Mol. Imaging, 5:139-147 (2006).
"Vial", Retrieved from http://en.wikipedia.org/w/index.php?title=Vial&oldid=603936258 [Downloaded on May 20, 2014].
U.S. Appl. No. 13/529,239, Jul. 5, 2013 Non-Final Office Action.
U.S. Appl. No. 13/353,148, Oct. 17, 2013 Final Office Action.
U.S. Appl. No. 13/353,148, Sep. 11, 2013 Response to Non-Final Office Action.
U.S. Appl. No. 13/353,148, Jun. 20, 2013 Non-Final Office Action.
U.S. Appl. No. 12/096,254, Aug. 23, 2013 Non-Final Office Action.
U.S. Appl. No. 11/697,573, Oct. 17, 2013 Final Office Action.
U.S. Appl. No. 11/697,573, Sep. 4, 2013 Response to Non-Final Office Action.
U.S. Appl. No. 11/697,573, May 10, 2013 Non-Final Office Action.
U.S. Appl. No. 12/077,612, Aug. 30, 2013 Non-Final Office Action.
U.S. Appl. No. 14/300,106, filed Jun. 9, 2014.
U.S. Appl. No. 13/426,400, May 5, 2014 Non-Final Office Action.
U.S. Appl. No. 12/077,612, Mar. 21, 2014 Final Office Action.
U.S. Appl. No. 12/096,254, Mar. 21, 2014 Final Office Action.
Zheng, et al., "Ultrasonic measurement of depth-dependent transient behaviors of articular cartilage under compression", *Journal of Biomechanics*, 38:1830-1837 (2005).
Epstein-Barasg, et al., A microcomposite hydrogel for repeated on-demand ultrasound-triggered drug delivery, *Biomaterials*, 31(19):5208-5217 (2010).
Konofagou, et al., "Ultrasound-Induced Blood-Brain Barrier Opening", *Current Pharmaceutical Biotechnology*, 13(7):1332-1345 (2012).
Chen, et al., "The size of blood-brain barrier opening induced by focused ultrasound is dictated by the acoustic pressure", J. Cereb. Blood Flow Metab., 34:1197-1204 (2014).
Carman, et al., "Adenosine receptor signaling modulates permeability of the blood-brain barrier", *The Journal of Neuroscience*, 31(37):13272-13280 (2011).
Shinna, et al., "Realtime tissue elasticity imaging using the combined autocorrelation method", *J. Med. Ultrasonics*, 29(autumn):119-128 (2002).
U.S. Appl. No. 14/091,010, filed Nov. 26, 2013.
U.S. Appl. No. 12/096,254, Dec. 23, 2013 Response to Non-Final Office Action.
U.S. Appl. No. 12/096,254, Dec. 17, 2013 Applicant Initiated Interview Summary.
U.S. Appl. No. 12/077,612, Jan. 30, 2014 Response to Non-Final Office Action.
U.S. Appl. No. 12/077,612, Jan. 2, 2014 Applicant Initiated Interview Summary.
U.S. Appl. No. 13/529,239, Dec. 31, 2013 Final Office Action.
U.S. Appl. No. 13/529,239, Dec. 3, 2013 Response to Non-Final Office Action.
U.S. Appl. No. 13/529,239, Nov. 18, 2013 Applicant Initiated Interview Summary.
U.S. Appl. No. 11/433,510, Jul. 23, 2014 Issue Fee Payment.
U.S. Appl. No. 11/433,510, Apr. 23, 2014 Notice of Allowance.
U.S. Appl. No. 11/433,510, Apr. 7, 2014 Applicant Initiated Interview Summary.
U.S. Appl. No. 11/433,510, Apr. 4, 2014 Response to Non-Final Office Action.
U.S. Appl. No. 11/433,510, Oct. 4, 2013 Non-Final Office Action.
U.S. Appl. No. 11/697,573, Jan. 12, 2015 Notice of Abandonment.
U.S. Appl. No. 11/697,573, Jun. 16, 2014 Non-Final Office Action.
U.S. Appl. No. 11/697,579, Nov. 28, 2011 Notice of Abandonment.
U.S. Appl. No. 11/899,004, Nov. 3, 2011 Decision on Petition.
U.S. Appl. No. 11/899,004, Sep. 19, 2011 Decision on Petition.
U.S. Appl. No. 12/077,612, Oct. 29, 2015 Notice of Abandonment.
U.S. Appl. No. 12/077,612, Apr. 9, 2015 Non-Final Office Action.
U.S. Appl. No. 12/096,254, Sep. 28, 2015 Notice of Abandonment.
U.S. Appl. No. 12/096,254, Feb. 27, 2015 Non-Final Office Action.
U.S. Appl. No. 12/096,254, May 31, 2012 Final Office Action.
U.S. Appl. No. 12/096,254, Apr. 4, 2012 Response to Non-Final Office Action.
U.S. Appl. No. 13/019,029, Mar. 21, 2013 Issue Fee payment.
U.S. Appl. No. 13/353,148, Aug. 12, 2015 Non-Final Office Action.
U.S. Appl. No. 13/353,148, Jul. 6, 2015 Amendment and Request for Continued Examination (RCE).
U.S. Appl. No. 13/353,148, Mar. 3, 2015 Final Office Action.
U.S. Appl. No. 13/353,148, Oct. 24, 2014 Response to Non-Final Office Action.
U.S. Appl. No. 13/353,148, Oct. 14, 2014 Applicant Initiated Interview Summary.
U.S. Appl. No. 13/353,148, Apr. 17, 2014 Amendment and Request for Continued Examination (RCE).
U.S. Appl. No. 13/353,148, Feb. 25, 2014 Applicant Initiated Interview Summary.
U.S. Appl. No. 13/353,148, Apr. 24, 2014 Non-Final Office Action.
U.S. Appl. No. 13/426,400, Dec. 4, 2015 Applicant Initiated Interview Summary.
U.S. Appl. No. 13/426,400, Dec. 4, 2015 Response to Non-Final Office Action.
U.S. Appl. No. 13/426,400, Jul. 2, 2015 Non-Final Office Action.
U.S. Appl. No. 13/426,400, Mar. 23, 2015 Amendment and Request for Continued Examination (RCE).
U.S. Appl. No. 13/426,400, Dec. 23, 2014 Final Office Action.
U.S. Appl. No. 13/426,400, Oct. 2, 2014 Response to Non-Final Office Action.
U.S. Appl. No. 13/529,239, Jun. 4, 2015 Final Office Action.

(56) References Cited

OTHER PUBLICATIONS

U.S. Appl. No. 13/529,239, Mar. 5, 2015 Applicant Initiated Interview Summary.
U.S. Appl. No. 13/529,239, Mar. 3, 2015 Response to Non-Final Office Action.
U.S. Appl. No. 13/529,239, May 1, 2014 Applicant Initiated Interview Summary.
U.S. Appl. No. 13/529,239, Jun. 30, 2014 Amendment and Request for Continued Examination (RCE).
U.S. Appl. No. 13/529,239, Sep. 3, 2014 Non-Final Office Action.
Chen, et al., "Architectural Acoustics and Noise: Advancements and Best Practices in Instrumentation for Architectural Acoustics and Noise", J. Acoust. Soc. Am.; 164th Meeting: Acoustical Society of America, 132(3, Pt. 2):1977-2018 (Sep. 2012).
Chen, et al., "Engineering Acoustics and ASA Committee on Standards: Sound Intensity Measurements", J. Acoust. Soc. Am.; 164th Meeting: Acoustical Society of America, 132(3, Pt. 2):1984 (Sep. 2012).
Cobbold, R.S.C., "Foundations of biomedical ultrasound", Biomedical engineering series, Oxford University Press, pp. 422-423(2006).
Damianou, et al., "Dependence of ultrasonic attenuation and absorption in dog soft tissues on temperature and thermal dose", J Acoust Soc Am, 102(1):628-634 (1997).
De Craene, et al., "Temporal diffeomorphic free-form deformation: Application to motion and strain estimation from 3D echocardiography", Medical Image Analysis, 16(2):427-450 (2012).
Definition of "spatial filter" retrieved from http://ww.onelook.com/ on May 26, 2015.
DuBose, et al., "Confusion and Direction in Diagnostic Doppler Sonography", Journal of Diagnostic Medical Sonography, 25(3):173-177 (2009).
Duerinckx, et al., "In vivo acoustic attenuation in liver: correlations with blood tests and histology", Ultrasound Imaging, 14(5):405-413 (1988).
Fenster, et al., "Three-dimensional ultrasound imaging", Phys Med Biol, 46(5):R67-R99 (2001).
Fujii, et al., "A new method for attenuation coefficient measurement in the liver", Journal of Ultrasound Medicine, 21(7):783-788 (2002).
Ginat, et al., "High-resolution ultrasound elastography of articular cartilage in vitro", Proceedings of the 28th IEEE EMBS Annual International Conference, New York City, USApp. 6644-6647 (Aug. 30-Sep. 3, 2006).
Housden, et al., "Ultrasonic imaging of 3D displacement vectors using a simulated 2D array and beamsteering", Ultrasonics, 53(2):615-621 (2013).
Hsu, et al., "Noninvasive and targeted gene delivery into the brain using microbubble-facilitated focused ultrasound", PLoS One 8(2): e57682 (Feb. 2013).
Jasaityte, et al., "Current state of three-dimensional myocardial strain estimation using echocardiography", J Am Soc Echocardiogr., 26(1):15-28 (2013).
Kawabata, et al., "Chemo-thermal approach for efficient ultrasonic tumor treatment with phase change nano droplet", IEEE Int. Ultrasonics Symp., Oct. 18-21, 2011 Orlando, Florida, pp. 9-12.
Kim, et al., "Multifunctional microbubbles and nanobubbles for photoacoustic and ultrasound imaging", J Biomed Opt., 15(1): 010510-1-010510-3 (Jan./Feb. 2010).
Konofagou, et al., "Noninvasive electromechanical wave imaging and conduction-relevant velocity estimation in vivo", Ultrasonics, 50(2):208-215 (2010).
Otani, "Use of ultrasound imaging to map propagating action potential waves in the heart", Computers in Cardiology, 36:617-620 (2009).
Palmeri, et al., "Characterizing acoustic attenuation of homogeneous media using focused impulsive acoustic radiation force", Ultrason Imaging, 28(2):114-128 (2006).
Papadakis, Emmauel P., "Ultrasonic Instruments & Devices", Academic Press, 8 pages (1999).
Provost, et al., "Imaging the electromechanical activity of the heart in vivo", PNAS, 108(21):8565-8570 (2011).
Provost, et al., "Mapping of cardiac electrical activation with electromechanical wave imaging: An in silico-in vivo reciprocity study", Heart Rhythm., 8(5):752-759 (2011).
Techavipoo, et al., "Temperature dependence of ultrasonic propagation speed and attenuation in excised canine liver tissue measured using transmitted and reflected pulses", The Journal of Acoustical Society of America, 115(6):2859-2865 (2004).

* cited by examiner

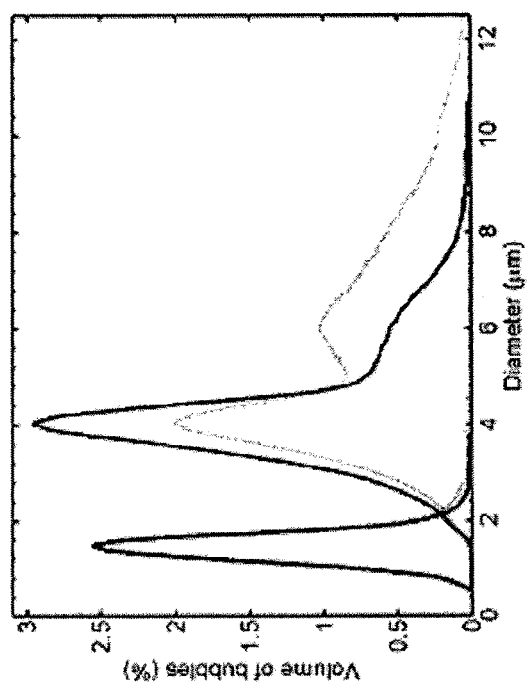
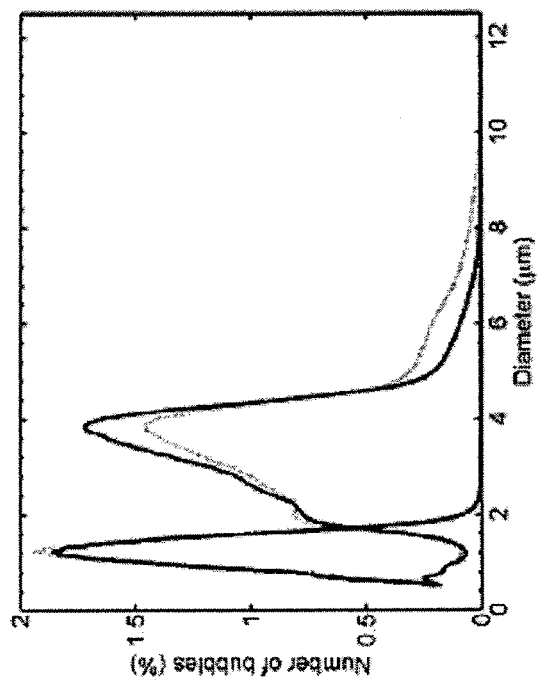
Figure 5(a)
Figure 5(b)

(a)

(b)

(c)

(d)

SYSTEMS AND METHODS FOR OPENING A TISSUE

CROSS REFERENCE TO RELATED APPLICATIONS

This application is a continuation-in-part of International Patent Application No. PCT/US2009/056565 entitled "Systems And Methods For Opening A Tissue", filed Sep. 10, 2009, which claims priority to U.S. Provisional Application No. 61/095,942 entitled "Molecular Delivery Using Focused Ultrasound", filed on Sep. 10, 2008, and U.S. Provisional Application No. 61/377,586 entitled "Effect of Microbubble Size on Fundamental Mode High Frequency Ultrasound Imaging in Mice", filed Aug. 27, 2010, each of which is incorporated by reference in its entirety herein and from which priority is claimed.

STATEMENT REGARDING FEDERALLY-SPONSORED RESEARCH

This invention was made with government support under R21 EY018505, R01 EB009041, R01-EB009066 and R21-CA139173 awarded by the National Institutes of Health, and CAREER 0644713 awarded by the National Science Foundation. The government has certain rights in the invention.

BACKGROUND

1. Field

The present application relates to systems and methods for opening a tissue utilizing microbubbles.

2. Background Art

The exchange of molecules across the cerebral microvasculature is strictly regulated by a unique interface known as the blood-brain barrier (BBB). Its primary function is to strictly regulate the brain's environment in order to prevent toxins from entering the parenchyma and maintain molecular environments necessary for proper neuronal firing. The result is the effective exclusion of nearly all systemically administered compounds larger than 400 Da (Daltons) from the brain's extracellular space, rendering many neurologically potent compounds ineffective. So, potential therapeutic agents, such as inhibitors (~1 kDa) and antibodies (30 to 300 kDa), will not reach their intended targets if administered systemically. Until a method to deliver such large agents in the brain at a critical dose is shown to be effective, advances in the treatment of central nervous system (CNS) disorders will remain impaired.

Focused ultrasound (FUS) applied after the systemic injection of ultrasound contrast agents (UCA) can open the BBB noninvasively. This method can concurrently deliver agents to the brain through the intact skull, locally (to a targeted volume), and transiently with the BBB closing within hours of its opening. In the past, assessment of safety has involved histological analysis to determine the presence of apoptosis, neuronal death, and erythrocyte extravasations, and magnetic resonance imaging (MRI) to determine the presence of hemorrhage, macroscopic structural changes, and the timeline of BBB closure. Comprehensive histological analyses of the damage within a few days of sonication has revealed that at specific acoustic parameters (i.e., frequency, pulse length, pulse repetition frequency, and duration) and pressures, BBB opening can occur without widespread hemorrhage or neuronal damage. Other concerns include the presence of small erythrocyte extravasations and the potential of delayed long-term effects that would not be visible in the mostly acute histological evaluations performed. However, the FUS-induced BBB opening results were reproduced in old APP/PS1 Alzheimer's mice where subsequent BBB closure was observed. There is a shortage of effective treatments of CNS diseases and, thereby, a pressing need for a brain drug delivery technique. In light of this need and the lack of clinical options, the safety levels of FUS-induced BBB opening are promising for human applications.

In terms of efficacy, FUS-induced BBB opening can increase the BBB's permeability to therapeutically-relevant-sized agents, such as Omniscan™ (573 Da), Magnevist® (938 Da), Evans Blue, Trypan Blue, Herceptin (148 kDa), doxorubicin (544 Da), and rabbit anti-Aβ antibodies. However, the magnitude of this permeability increase, the spatial distribution of the trans-BBB delivered agents within the targeted volume, and the dependence of both on the molecular weight of the delivered compounds have not been extensively investigated. In order to study these characteristics, dextrans at three distinct molecular weights (3, 70, and 2000 kDa) have been employed as model agents. Although compounds larger than 400 Da can be delivered, a size exclusion threshold remains. For example, a 3 kDa dextran has been delivered more diffusely and at a higher concentration than a 70 kDa dextran. Dextrans have also been deposited at larger amounts proximal to larger vessel branches such as the internal and external transverse hippocampal vessels, and the vessels within the thalamus, when compared to other regions in the targeted hippocampus. As a result, although large compounds can be delivered through the BBB, there remain concerns with the effective concentration and spatial distribution of trans-BBB delivered compounds.

FUS-induced BBB opening studies have used microbubble UCA's (e.g., Definity®, SonoVue®, and Optison™) that were either protein- or lipid-shelled with a stabilized gas core. A purpose of these UCA was to provide image contrast while remaining safe for systemic injection by restricting the administered bubble size to below 10 µm. FUS-induced BBB opening, in a stark contrast, involves pre-formed microbubbles to increase the BBB's permeability by opening, for example, the tight junctions or transcellular pathways to allow previously impermeable molecules to go through; in other words, to modulate the biological environment, albeit temporarily. At the low acoustic pressures often used in FUS-induced BBB opening (<1 MPa peak-rarefactional), microbubbles are an important component since opening may not occur without its presence in the vasculature.

Accordingly, there is a need in the art for techniques for opening the BBB in a safe and localized manner.

SUMMARY

Systems and methods for opening a tissue to a target value are disclosed herein. In an exemplary method, a region of the tissue is targeted for opening, a size range of microbubbles corresponding to the target value is determined, microbubbles of the size range are positioned in proximity to the targeted region, and an ultrasound beam is applied to the targeted region such that the tissue is opened with the assistance of the microbubbles to the target value.

The method can include determining a concentration range of microbubbles corresponding to the target value and positioning microbubbles of that concentration range in proximity to the targeted region. The method can also include determining a pressure range for the ultrasound beam corresponding to the target value and applying the ultrasound beam at that pressure range. In some embodiments the pressure range corresponds to a resonance frequency of the microbubbles proximate to the targeted region. The method can further include applying an ultrasound beam to move the microbubbles into vessels of the tissue.

The determination of the size range of microbubbles can include determining a size range corresponding to a size range of vessels the tissue. The size range of microbubbles can be 4 to 5 microns or 1 to 2 microns or 9 to 10 microns or 6 to 8 microns in some embodiments. Further, the microbubbles can be acoustically activated microbubbles and can also be molecule carrying microbubbles. The molecule carrying microbubbles can carry medicinal molecules and/or a contrast agent and/or a biomarker and/or a liposome. Medicinal molecules and/or contrast agents can also be separately positioned in proximity to the targeted region.

A method for imaging the opening of a tissue to a target permeability is also disclosed herein and includes targeting a region of the tissue for opening, determining a size range of microbubbles corresponding to the target value, positioning microbubbles of the size range in proximity to the targeted region, applying an ultrasound beam to the targeted region such that the tissue is opened with the assistance of the microbubbles to the target value, and collecting image information for the targeted region of the opened tissue. In some embodiments imaging the targeted region includes applying an ultrasound beam to the targeted region, while in other embodiments imaging the targeted region comprises utilizing a magnetic resonance imaging device to image the targeted region.

An exemplary system for opening a tissue to a target value using a solution of size-controlled microbubbles having a size range corresponding to said target value includes a targeting assembly for targeting a region of the tissue, an introducer adapted to deliver the solution to a location proximate to the targeted region, and a transducer, coupled to said targeting assembly, adapted to apply an ultrasound beam to the targeted region thereby opening the tissue with the assistance of the microbubbles to the target value. In some embodiments, the targeting assembly includes an ultrasound transducer and/or at least one member for placement on an anatomical landmark corresponding to the target region.

A system for imaging the opening of a tissue to a target value using a solution of size-controlled microbubbles includes a targeting assembly for targeting a region of the tissue, an introducer adapted to deliver the solution to a location proximate to the targeted region, a transducer, coupled to said targeting assembly, adapted to apply an ultrasound beam to the targeted region to thereby open the tissue with the assistance of the microbubbles to the target value, an imaging device adapted to capture image data of the opened tissue of the targeted region, and a processor, operatively coupled to said imaging device, adapted to process the image data to form an image therefrom. In some embodiments, the imaging device includes a transducer, while in other embodiments the imaging device includes a magnetic resonance imaging device.

BRIEF DESCRIPTION OF THE DRAWINGS

The accompanying drawings, which are incorporated and constitute part of this disclosure, illustrate some embodiments of the disclosed subject matter.

FIG. 5(a) illustrates the size distribution of microbubbles as the number-weighted percentage of the total concentration of bubbles in accordance with an exemplary embodiment of the disclosed subject matter.

FIG. 5(b) illustrates the size distribution of microbubbles as the volume-weighted percentage of the total volume of bubbles in accordance with an exemplary embodiment of the disclosed subject matter.

Throughout the figures and specification the same reference numerals are used to indicate similar features and/or structures.

DETAILED DESCRIPTION

The systems and methods described herein are useful for opening a tissue utilizing microbubbles and focused ultrasound. Although the description is focused on the example of opening the blood-brain barrier, the systems and methods herein are useful for opening other tissues, such as muscular tissue.

The subjected matter disclosed herein are methods and systems for determining size ranges of microbubbles for opening a tissue to allow for the passage of certain molecules over selected areas. Accordingly, the techniques described herein make use of selected size ranges of microbubbles chosen to produce a desired opening effect in a tissue when subjected to focus ultrasound in a selected range of acoustic pressures.

Figure 1:
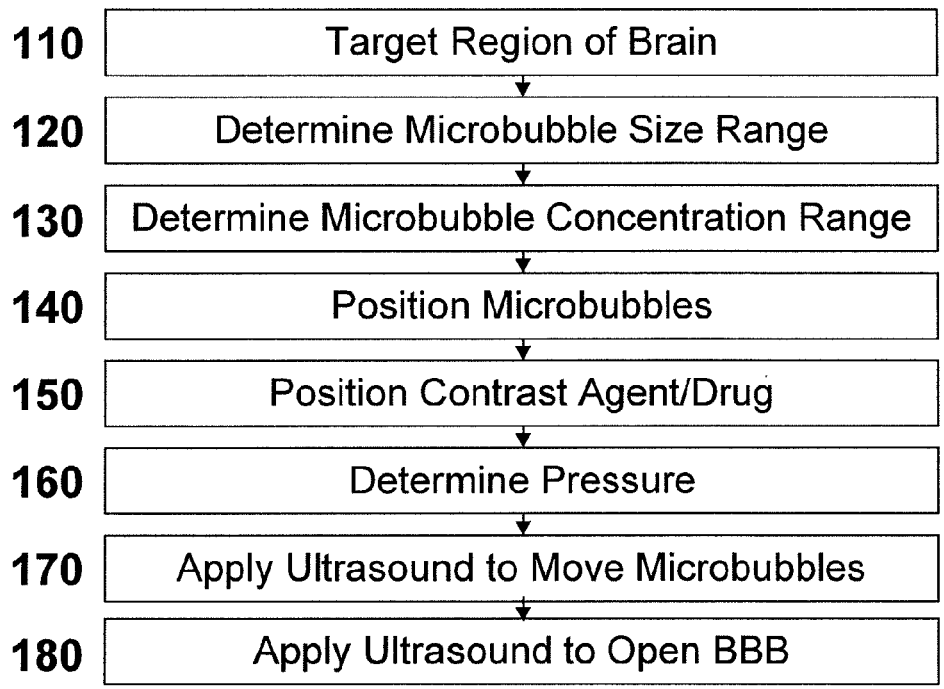
FIG. 1 illustrates a method for opening a blood-brain barrier in a brain of a subject to a target permeability in accordance with an exemplary embodiment of the disclosed subject matter.

FIG. 1 illustrates a method 100 for opening a tissue to a target value, e.g., a measure of increased ability of the tissue to pass through molecules. The target value can be expressed in terms of an increase in the size of vessels in the tissue, as an area of the tissue that has been opened, or in terms of a rate at which molecules pass through, e.g., a permeability, or as a combination of any of these measures. The method 100 involves targeting 110 a region of the tissue for opening, determining 120 a size range of microbubbles corresponding to the target value, positioning 140 microbubbles of the size range in proximity to the targeted region, and applying 180 an ultrasound beam to the targeted region such that the tissue is opened with the assistance of the microbubbles to the target value.

As illustrated in FIG. 1, in one exemplary embodiment, the method 100 can further include of determining 130 a concentration range of microbubbles corresponding to the target value and the positioning 140 of the microbubbles can also include positioning the microbubbles of the concentration range that corresponds to the target value. The method 100 can also include positioning 150 a contrast agent and/or medicinal molecule (e.g., a drug) in proximity to the target region. In the same or another embodiment, the method 100 can further include determining 160 a pressure range for the ultrasound beam that corresponds to the target value of the tissue and applying 180 the ultrasound beam can include applying the ultrasound beam in the determined pressure range.

In one exemplary embodiment, method 100 can include applying 170 an ultrasound beam to move the microbubbles into vessels of the tissue. This application 170 of the ultrasound beam can be the same, or a different, application 180 that is used to open the tissue. Further, the application 170 of the ultrasound beam can be in the same, or a different, pressure range than that determined 160 for the purposes of opening the tissue.

Figure 2:
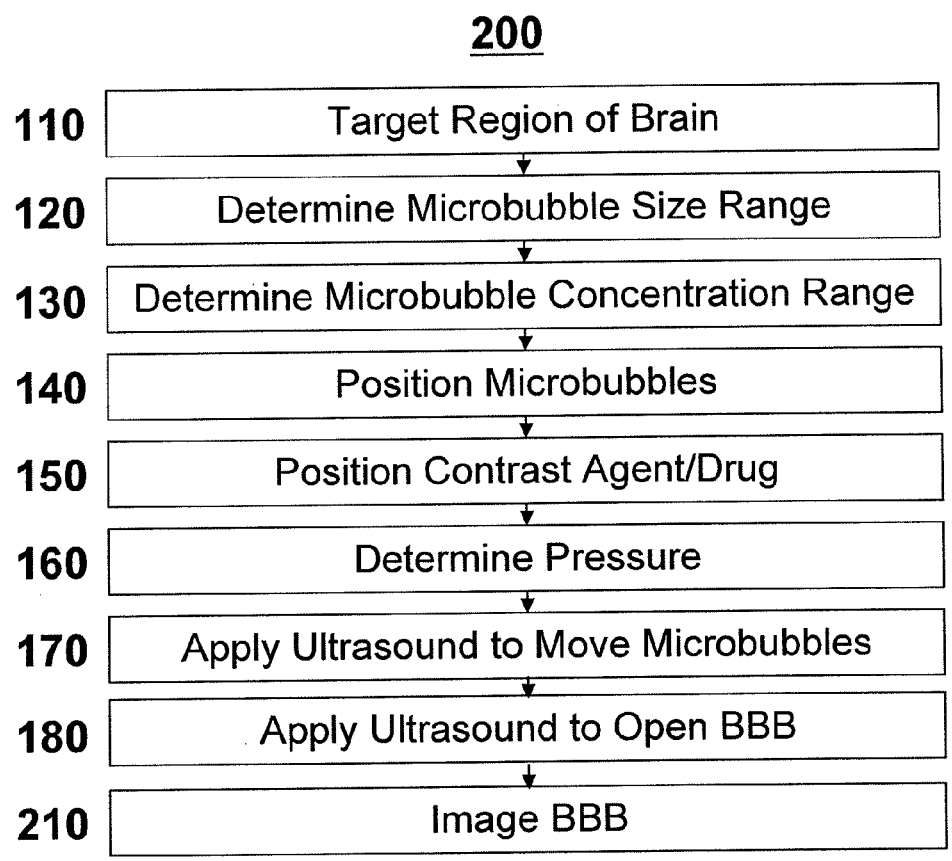
FIG. 2 illustrates a method for imaging the opening of a blood-brain barrier in a brain of a subject to a target permeability in accordance with an exemplary embodiment of the disclosed subject matter.

FIG. 2 illustrates a method 200 in accordance with the disclosed subject matter for imaging the opening of a tissue. The method 200 includes the same basic techniques for opening the tissue to a target value: targeting 110 a region of the tissue for opening, determining 120 a size range of microbubbles corresponding to the target value, positioning 140 microbubbles of the size range in proximity to the targeted region, and applying 180 an ultrasound beam to the targeted region such that the blood-brain barrier is opened with the assistance of the microbubbles to the target value. The method 200 further includes imaging 210 the opened tissue. In some embodiments, imaging 210 the opened tissue can be the same as the application 180 of an ultrasound beam to open the tissue. In another embodiment, imaging 210 can include utilizing an MRI device to image the opening of the tissue.

Figure 3A:
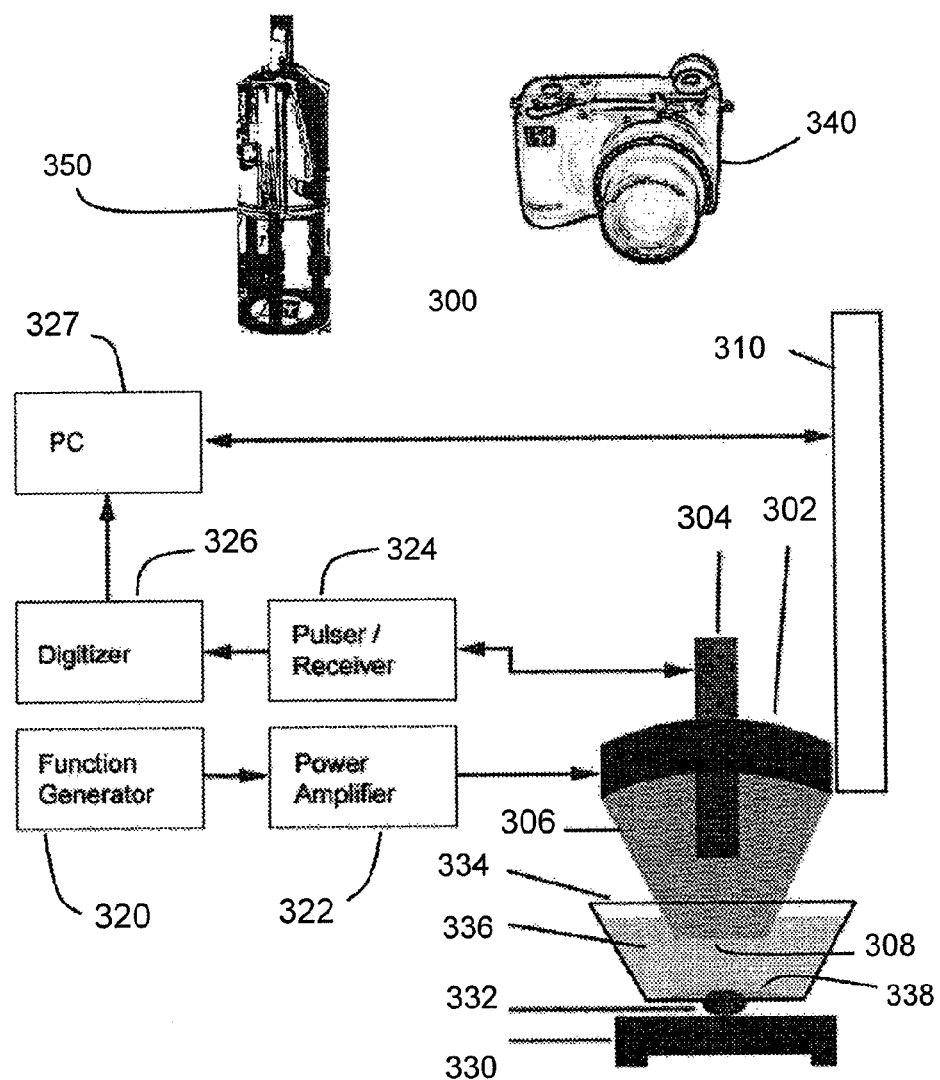
FIG. 3(a) illustrates a system for opening and/or imaging the opening of a blood-brain barrier in a brain of a subject to a target permeability in accordance with an exemplary embodiment of the disclosed subject matter.

FIG. 3(a) illustrates a system 300 for opening a tissue to a target value. System 300 has many of the same features as the system described in U.S. Patent Pub. No. 2009/0005711, a commonly assigned patent application which is incorporated by reference in its entirety herein. Ultrasound waves are generated by a focused ultrasound transducer (FUS) 302, which can be a single-element circular-aperture FUS transducer. In one exemplary embodiment the FUS transducer 302 can be a single-element, spherical segment FUS transducer with center frequency of 1.525 MHz, a focal depth of 90 mm, an outer radius of 30 mm, and an inner radius of 11.2 mm (Riverside Research Institute, New York, N.Y., USA). The FUS transducer can be provided with hole in its center for receipt of an imaging transducer 304, which can be a single-element diagnostic transducer having a center frequency of 7.5 MHz with a focal length of 60 mm (Riverside Research Institute, New York, N.Y., USA). The FUS transducer 302 and the diagnostic transducer 304 can be positioned so that the foci of the two transducers are properly aligned, e.g., overlap.

Further illustrated in FIG. 3(a), an exemplary system 300 can include a cone 306 filled with degassed and distilled water and mounted on system 300. The cone 306 can, for example, be manufactured from a clear plastic, such as polyurethane. The water is contained in the cone 306 by capping it with a material considered substantially "transparent" to the ultrasound beam, such as an ultrathin polyurethane membrane 308 (Trojan; Church & Dwight Co., Princeton, N.J., USA).

The transducer assembly, which can include the FUS transducer 302 and the diagnostic transducer 304, can be mounted to a computer-controlled 3-D positioning system 310 (Velmex Inc., Lachine, QC, Canada), including motors VXM-1 and VXM-2 used in the exemplary embodiment. It is understood that other positioning systems can be incorporated for positioning the transducer assembly with respect to the targeted tissue.

In the same or another exemplary embodiment, the FUS transducer 302 can be driven by a function generator 320, e.g., function generator HP33150A, manufactured by Agilent Technologies, Palo Alto, Calif., USA, through an amplifier 322, such as a 50-dB power amplifier 3100L (ENI, Inc., Rochester, N.Y., USA). The diagnostic transducer 304 can be driven by a pulser-receiver system 342, for example a pulser-receiver 5052PR (Panametrics, Waltham, Mass., USA), connected to a digitizer 326, e.g., digitizer CS14200 (Gage Applied Technologies, Inc., Lachine, QC, Canada). It is understood that the above-described components can be modified or replaced with other components, as is known in the art, for producing the ultrasound beams described herein. Computer 328 typically includes a processor, such as a CPU (not shown), and can be any appropriate personal computer or distributed computer system including a server and a client. For example, a computer useful for this system is a Dell Precision 380 personal computer. It is understood that any personal computer, laptop, or other processor that can load software and communicate with the various components discussed herein can be used. A memory unit (not shown), such as a disk drive, flash memory, volatile memory, etc., can be used to store software for positioning and operating the transducer assembly, image data, a user interface software, and any other software which can be loaded onto the CPU.

Figure 3B:
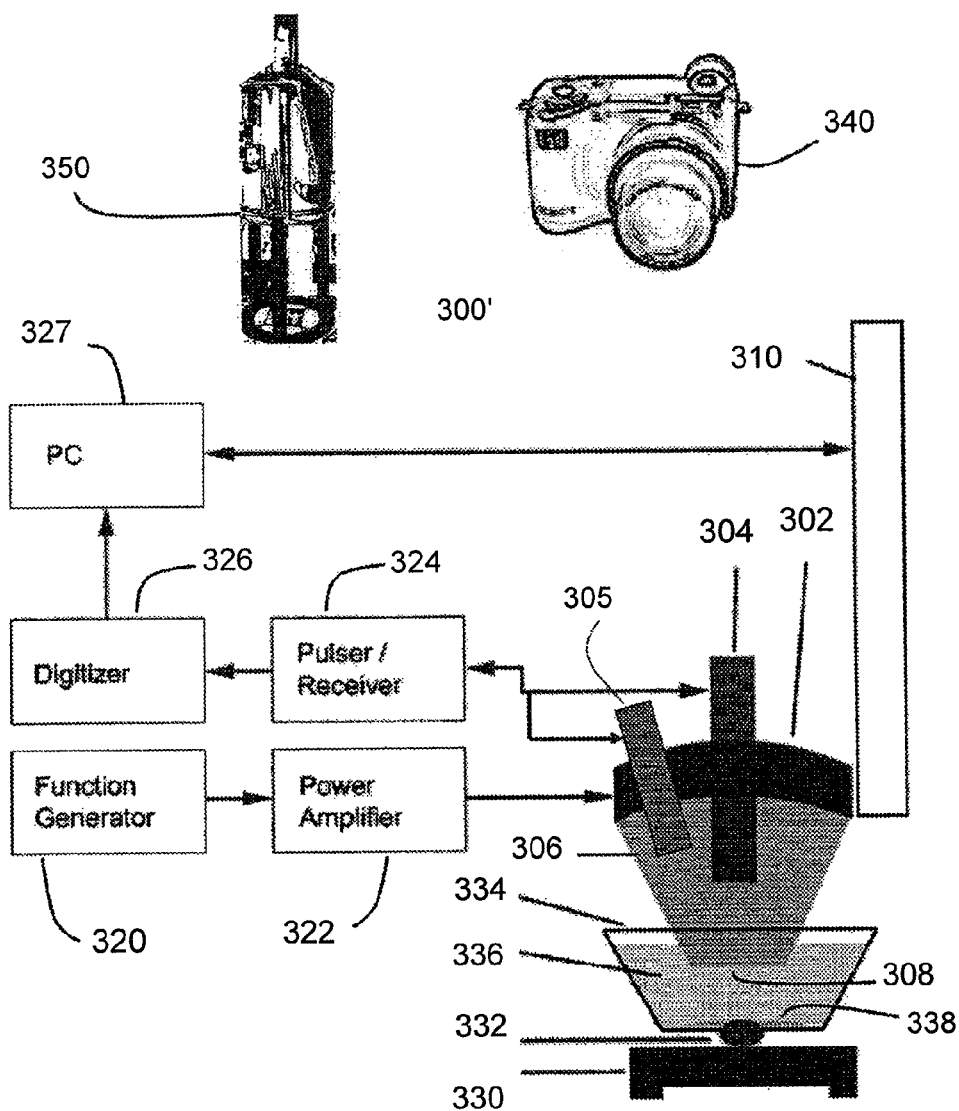
FIG. 3(b) illustrates another system for opening and/or imaging the opening of a blood-brain barrier in a brain of a subject to a target permeability in accordance with an exemplary embodiment of the disclosed subject matter.

In another exemplary embodiment illustrated in FIG. 3(b), system 300' can include a transducer assembly having an array of a plurality of single-element FUS transducer 304 and 305 which can be targeted to different regions of the brain of the subject. Each FUS transducer 304, 305 in the array can be fired individually, thereby permitting opening of the BBB in several locations without repositioning the transducer assembly.

Prior to sonication and in order to verify undistorted propagation through the skull, a scan, such as a 3-D raster-scan (lateral step size: 0.2 mm; axial step size: 1.0 mm), of the beam of the FUS transducer 302, can optionally be performed in a large water tank containing degassed water with a needle hydrophone having a needle diameter on the order of about 0.2 mm (Precision Acoustics Ltd., Dorchester, Dorset, UK). In this manner the pressure amplitudes and three-dimensional beam dimensions of the FUS transducer 302 can be measured. The pressure amplitudes can be measured by calculating the peak-rarefactional pressure values and accounting for a pressure attenuation due to transcranial propagation, e.g., an 18% pressure attenuation. The dimensions of the beam provided by the FUS transmitter 302 can have a lateral and axial full-width at half-maximum (FWHM) intensity of approximately 1.32 and 13.0 mm, respectively, and in some embodiments can be approximately equal to the dimensions of the beam after propagation through the skull.

System 300 also includes a liquid container 334 containing an appropriate liquid 336, e.g., degassed and distilled water, which is sealed at the bottom with a membrane 338, which can be a polyurethane membrane that is acoustically and transparent, e.g., plastic wrap. The system 300 can also include an optical imaging device 340, such as a digital camera, for imaging the skull of the subject 332 and a MRI device 350 for imaging the brain of the subject 332.

System 300 also includes a platform 330 for the subject. In one exemplary embodiment, the platform 330 for the subject can be a polyurethane bed for a smaller subject 332, such as a mouse. In this configuration, the membrane 338 can be placed over the subject 332. In other embodiments, the platform 330 can be a hospital bed or surgical table, in which a larger subject 332 (such as a human subject) can be laid prone or supine and the transducer assembly positioned on top of the region of the skull targeted.

Figure 4A:
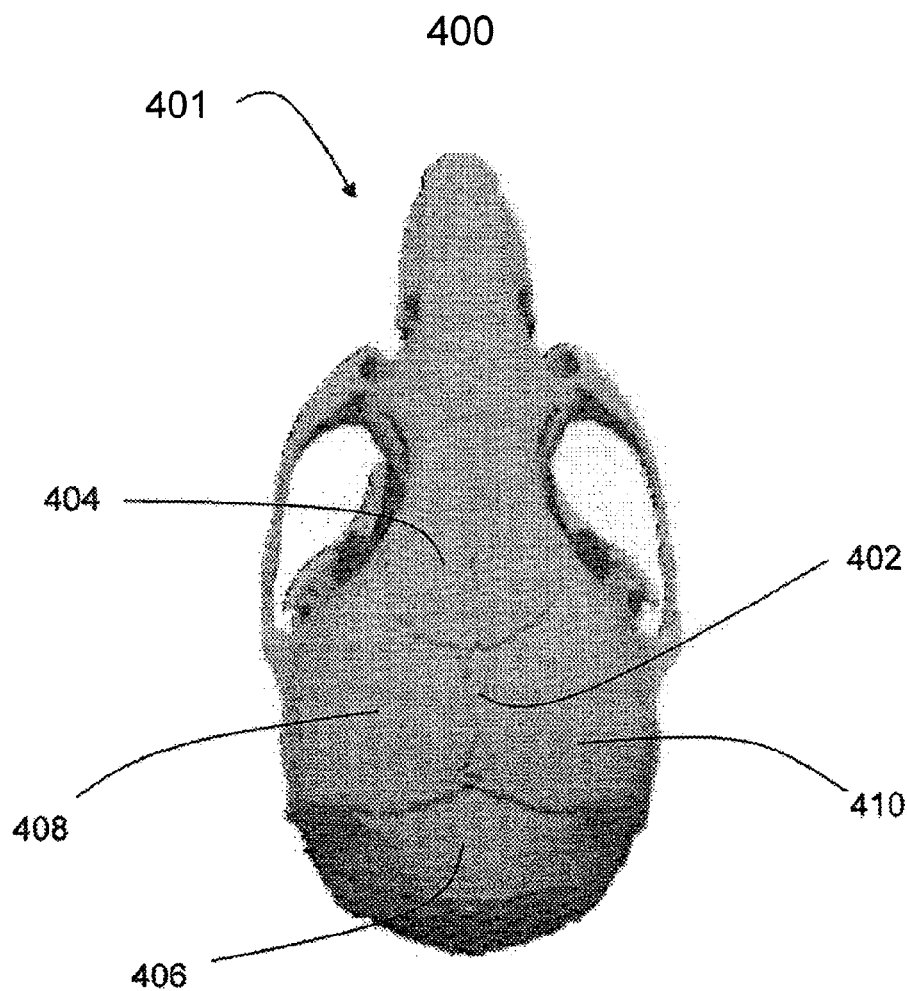
FIGS. 4(a)-(e) illustrate a targeting system for locating a target region of the brain of a subject in accordance with an exemplary embodiment of the disclosed subject matter.

Additional components of the system 300 include a targeting system 400, coupled to the FUS transducer 302, for locating the focus of the FUS transducer 302 in the brain of the subject 332. The targeting system 400 can be coupled by any known method that permits the targeting system 400 to aid in properly targeting the FUS transducer 302 to the region of interest for opening of the target tissue, e.g., acoustic and/or optical coupling. FIGS. 4(a)-(d) illustrate a targeting system 400 for use with an embodiment where the subject 332 is a mouse. FIG. 4(a) illustrates mouse skull 401, where the skull's sutures can be seen through the skin and used as anatomic landmarks for targeting purposes. As illustrated in FIG. 4(a), the landmarks of mouse skull 401 include the sagittal suture 402, the frontal bone 404, the interparietal bone 406, the left parietal bone 408, and the right parietal bone 410.

Figure 4B:
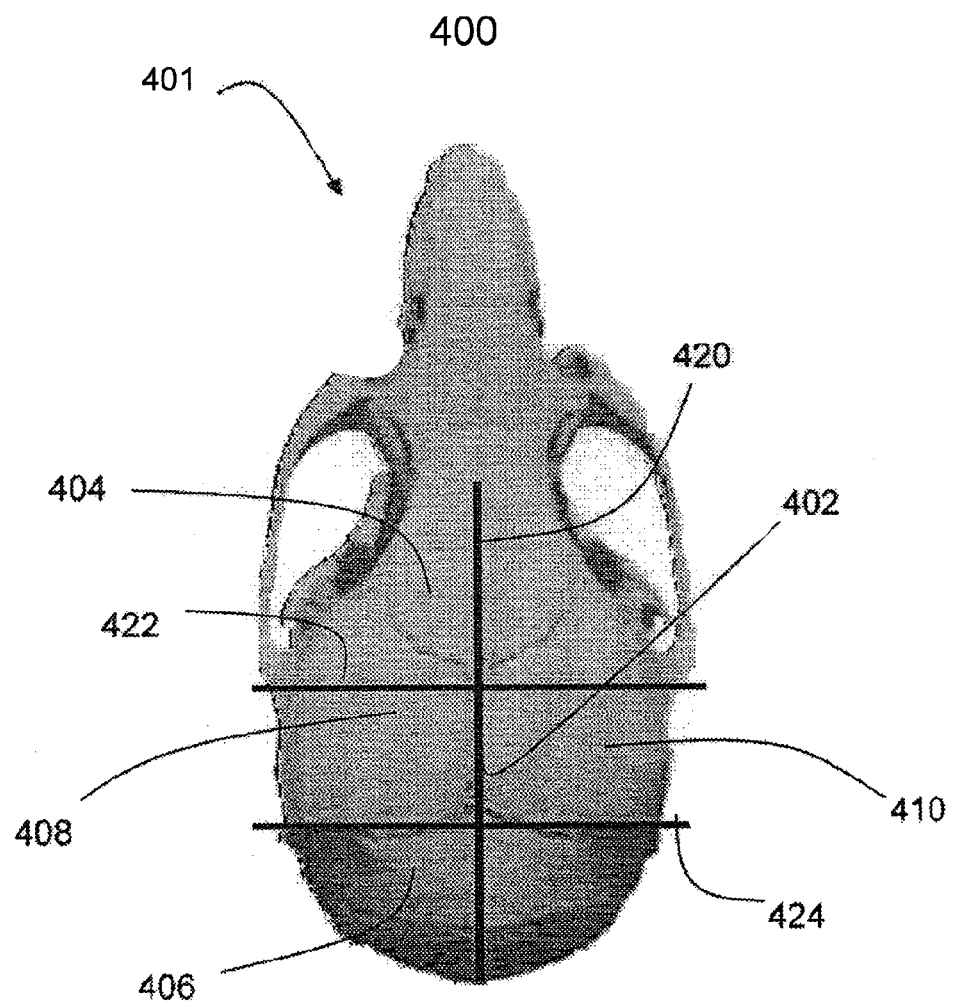

FIG. 4(b) illustrates the placement of targeting system 400 on skull 401 in accordance with an exemplary embodiment. The targeting system 400 can include a plurality of members 420, 422, 424, such as thin metal bars, e.g., 0.3 mm thin metal bars, fabricated from an acoustically reflective material, e.g., paper clips. The metal bars 420, 422, 424 can be placed on several landmarks of the skull of the subject to create a layout, or grid. As illustrated in FIG. 4(b), a grid consisting of three equally spaced 0.3-mm thin F2 metal bars 420, 422, 424 was placed in the water bath 334 on top of the skull 401 and in alignment with these landmarks, e.g., bone sutures. The first bar 420 was aligned parallel and along the sagittal suture 402, and the second bar 424 was attached perpendicularly to the first bar and in alignment with the suture between the parietal 408 and interparietal bone 406. The third bar 422 was placed 4 mm away from and parallel to the second bar 424.

Figure 4C:
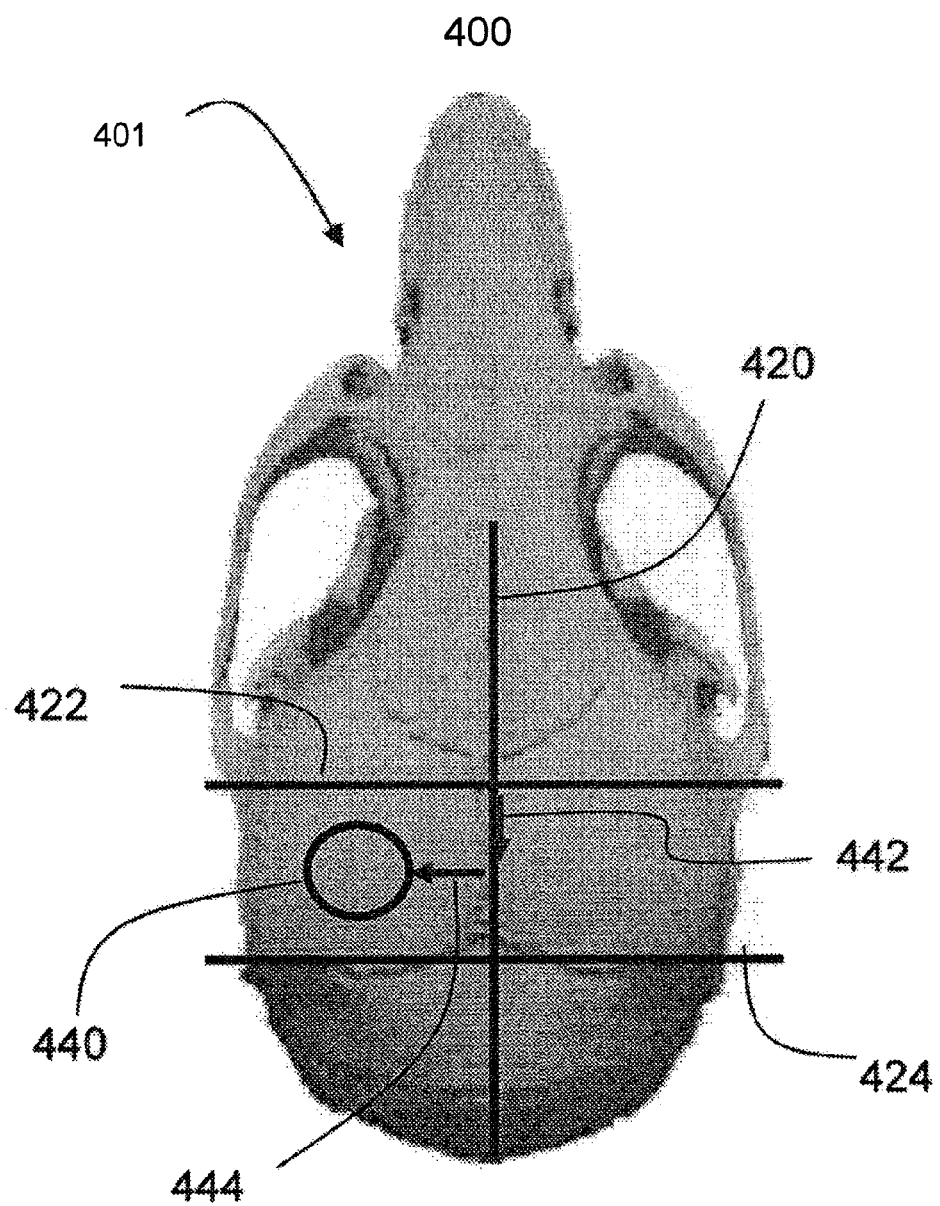

FIG. 4(c) illustrates the location of a brain structure 440 to be targeted, here the hippocampus, relative to the landmarks noted above. The location of the hippocampi are assumed relative to the sutures based on the mouse brain and known skull anatomy. In this exemplary embodiment, using the grid positioning system 400, the location of one of the hippocampi (indicated by circle 440) was reproducibly targeted when assumed to be at mid-distance (arrow 442) between the parallel bars 422, 424 and 2 mm away from the center bar 420 (arrow 444).

To locate the desired brain structure 440 an image, such as a lateral 2-D raster scan, of the grid configuration can be made using the diagnostic transducer 304. The focus of the FUS transducer 302 can then be positioned to precisely target the desired brain structure 440. In another exemplary embodiment, the targeting system can include other imaging devices, such as a digital camera 340. For example, a digital camera 340 can be used to photograph the head of the subject 332. The relevant landmarks can be identified in the photograph, and the focus of the FUS transducer 302 targeted to a location relative to the landmarks. In addition, other MRI targeting equipment, as is known in the art, can be used for targeting the desired brain structure 440 or other targeted tissue structure.

Figure 4D:
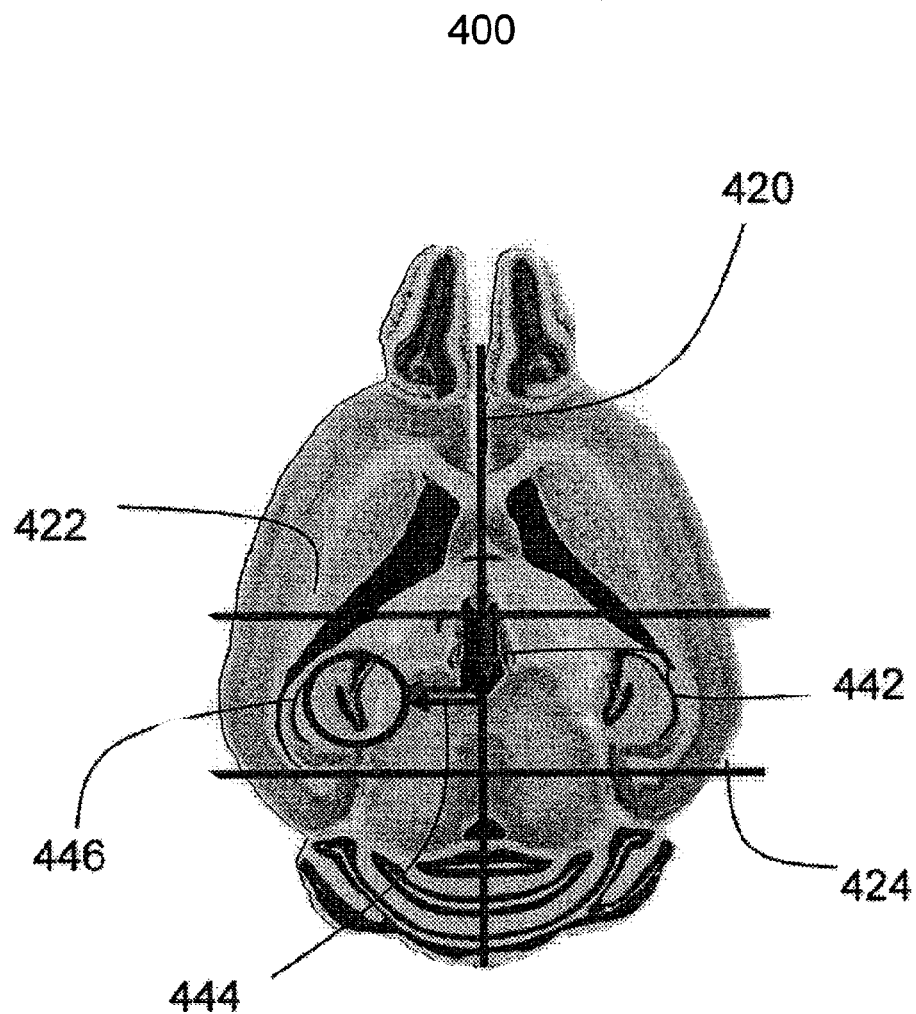
Figure 4E:
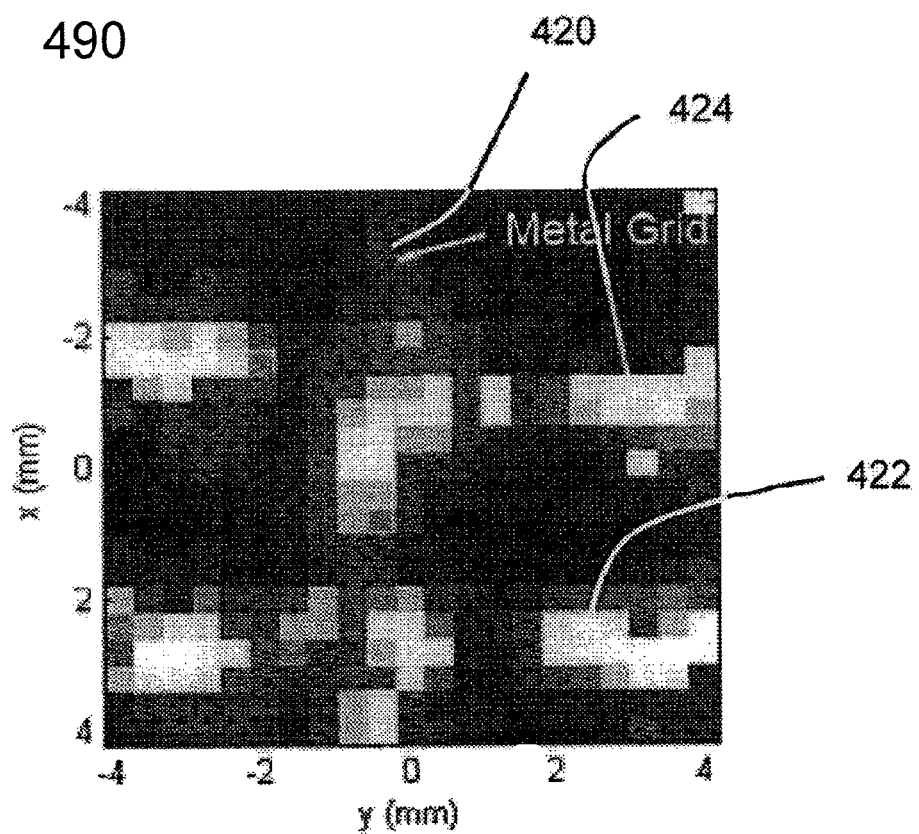

FIG. 4(d) illustrates the actual location of the hippocampus 446 as indicated in the histology slice. FIG. 4(e) illustrates a lateral 2-D raster-scan 490 of the grid 400 using the diagnostic transducer 304. The location of the hippocampus can be identified relative to this grid. The focus of the FUS transducer 302 was placed 3 mm beneath the top of the skull by measuring distance with the diagnostic transducer 304. Using the grid positioning system 400 and depth calculations, precise, accurate and reproducible targeting of the hippocampus or other brain structures can be performed. In one exemplary embodiment, the grid positioning system 400 allowed for sonication of the same location with good accuracy across different mice. This allowed for not only good reproducibility across different mice, but also a good comparison of BBB opening effects in different regions 440 within the sonicated area.

An exemplary method 100 for opening the BBB will be described in connection with the above-referenced figures. The subject 332 is positioned on a platform 330. Subject 332 can be positioned in a prone position, and can be anesthetized for the sonication procedure. The degassed and distilled water bath 334 is suspended over the subject's 332 head. Ultrasound gel can be used to reduce any remaining impedance mismatches between the thin plastic layer 338 and the subject's 332 skin. The transducer assembly can be placed in the water bath 334 with its beam axis perpendicular to the surface of the skull 401.

The focus of the transducer is positioned inside the subject's 332 brain. The focus can be targeted 110 to a region of the brain 440, such as the desired brain tissue, e.g., the hippocampus 446, or to the vasculature of the brain, e.g., arteries, ventricles, arterioles, and capillaries of the brain, or to other target tissue regions at different locations in the subject 332. The targeted region 440 of the brain can be located 110 utilizing the targeting system as discussed above.

Determination and production of the appropriate size and concentration ranges of microbubbles will now be described in connection with an exemplary embodiment. The appropriate size range of microbubbles can be determined 120 by comparing the bubble size to the cerebral vasculature size and selecting a bubble size that is small enough to perfuse the vessels while at the same time large enough to induce sufficient mechanical stress on the vessel walls, such that the vessels are opened to the target value.

The target value of the tissue can be selected based on the size of the molecule that is to pass through the tissue, e.g., the BBB, or based on the size, e.g., area, of the region that is to be exposed to the molecule, or a combination of the two. In one exemplary embodiment, microbubbles of 4-5 μm were determined 120 to be an appropriate size range for opening the BBB of mice to a target value which allowed for the passage of 3 kDa molecules into an area on the order of 2 mm. In another exemplary embodiment, 1-2 μm bubbles were determined 120 to be an appropriate size range for opening the BBB of mice to a target value which allowed for the passage of 3 kDa molecules in an area on the order of 1 mm. In other embodiments, size-isolated microbubbles in the range of 6-8 μm and/or 9-10 μm can be determined 120 to be an appropriate size range for opening the BBB. In one exemplary embodiment, the target value can be such that molecules up to the megaDalton size range are able to pass through the BBB, e.g., 2 MDa molecules.

In one exemplary embodiment, microbubbles including of a 1,2-Distearoyl-sn-glycero-3-phosphocholine (DSPC) and polyoxyethylene-40 stearate (PEG40S) lipid-shell and a perfluorobutane (PFB) gas core can be manufactured. In other exemplary embodiments, the microbubbles can be any type of microbubbles that capable of being acoustically activated, e.g., vibrated, such that they induce mechanical stress on the interior of a tissue vessel wall. Size-selected microbubbles can be isolated from a polydispersed microbubble distribution using a method described in International Patent Application No. PCT/US09/56513, a commonly assigned patent application which is incorporated by reference herein in its entirety. In brief, this method utilizes a two part procedure: acoustic emulsification and differential centrifugation.

Acoustic emulsification was used to generate a polydispersed microbubble distribution. A mixture of DSPC and PEG40S in filtered PBS was heated and its lipid aggregates were dispersed into smaller unilamellar liposomes by sonicating with a 20-kHz probe (Model 250A, Branson Ultrasonics; Danbury Conn., USA) at 3 W. PFB gas was then flowed over the surface of the lipid suspension. Microbubbles were then generated by sonicating the suspension at 33 W for about 10 s at the gas-liquid interface and collected in 30-mL syringes (Tyco Healthcare, Mansfield, Mass.). Subsequent washing and size fractionation was performed with a bucket-rotor centrifuge (Model 5804, Eppendorf, Westbury, N.Y.; radius: 16 cm from the center to the syringe tip; RPM: 10 to 14500 RPM). Microbubbles from the suspension were collected as a cake (portion of the centrifuged syringe located substantially radially inward) after centrifuging at 300 RCF for 10 min.

Differential centrifugation was used to isolate microbubbles of select 1-2, 4-5, or 6-8 μm diameter ranges. In each case, the initial microbubble size distribution of the cake was measured by laser light obscuration and scattering (Accusizer 780A, NICOMP Particle Sizing Systems, Santa Barbara, Calif.) to determine the relative centrifugal force (RCF) necessary for a microbubble size range to rise in the syringe column. Stokes' equation was used for the rise velocity of a buoyant particle relative to the bulk fluid under creeping flow conditions. Based on this equation, bubble suspensions were centrifuged at a specific RCF and duration whereby its resulting cake, or infranatant (portion of the centrifuged syringe located radially outward) was re-suspended to preserve either larger or smaller bubbles, respectively. The centrifugation and re-suspension process was repeated several times until the desired 1-2, 4-5, or 6-8 μm diameter range were obtained. The final cake was re-dispersed to a 1-mL volume of 20 vol % glycerol solution in PBS and stored in a 2-mL serum vial with PFB headspace.

In one example, 1-2 μm bubbles were isolated from an initial microbubble sample collected in 60 mL syringes. Microbubbles greater than 6 μm were removed by centrifuging the initial microbubble suspension at 50 RCF for 1 min. The infranatant containing smaller bubbles was re-suspended to 60 mL with PBS, while the cake containing larger bubbles was discarded. Microbubbles greater than 3 μm diameter were removed by centrifuging the collected infranatant at 290 RCF for 1 min. The infranatant was re-suspended to 60 mL with PBS, while the cake was discarded. The collected infranatant was concentrated down to 1 mL using 300 RCF for 5 min. The sample was stored in 2-mL serum vials. The final gas concentration of the suspension was at least 1 vol % to ensure stability.

Microbubbles in the 4-5 μm size range were isolated by first centrifuging the initial microbubble sample at 120 RCF for 1 min to remove bubbles less than 4 μm in diameter. The resulting cake was collected and reconstituted with PBS, while the infranatant was discarded. This washing was repeated five to seven times to fully remove smaller bubbles from the sample. Microbubbles greater than 6 μm were removed by centrifuging the resulting suspension at 80 RCF for 1 min. The infranatant containing 4-5 μm bubbles was collected, while the cake was discarded. The infranatant was re-suspended and centrifuged at 80 RCF for 1 min again to completely remove the larger bubbles. This size-isolation procedure was repeated two to three times to collect a sufficient number of microbubbles. The resulting cakes containing 4-5 μm bubbles were combined and concentrated to 1 mL. The final gas concentration of the 4-5 μm microbubble suspension ranged from 2-5 vol %.

Microbubbles in the 6-8 μm size range were isolated by first centrifuging the initial sample at 60 RCF for 1 min to remove bubbles smaller than 6 μm. The cake was collected and reconstituted with PBS, while the infranatant was discarded. This washing was repeated five to seven times to fully remove smaller bubbles from the sample. Microbubbles greater than 8 μm in diameter were removed by centrifuging the resulting suspension at 40 RCF for 1 min. The infranatant containing 6-8 μm bubbles was collected, while the cake was discarded. The infranatant was re-suspended and centrifuged at 40 RCF for 1 min to completely remove the larger bubbles. The size-isolation procedure was repeated two to three times to produce enough 6-8 μm bubbles for storage. The resulting cakes containing 6-8 μm bubbles were combined and concentrated to 1 mL. The final gas concentration of the 6-8 μm microbubble suspension ranged from 2-10 vol %.

The final microbubble size distribution in each vial was verified by laser light obscuration and scattering (Accusizer 780A, NICOMP Particle Sizing Systems, Santa Barbara, Calif.) before and after its use in the FUS-induced BBB opening experiments.

In one exemplary embodiment, it was shown that sonication of systemically administered 140 lipid-shelled bubbles isolated in separate diameter ranges of 1-2 and 4-5 μm can induce BBB opening in mice. It was further found that the pressure threshold for inducing BBB opening was lower in the presence of the 4-5 μm bubbles compared to the 1-2 μm bubbles. In fact, the fluorescence from trans-BBB delivered dextrans was greater for larger bubbles at every pressure amplitude tested. Apart from bubble size dependence, BBB opening was shown to be dependent on the brain region sonicated. Greater fluorescence was observed in the thalamus when compared to the hippocampus. Furthermore, preliminary histological evaluation indicated that custom, in-house manufactured, discrete size-isolated bubbles were not inducing any discrete damage sites at pressure amplitudes around the discovered threshold.

Thus, it was shown that in-house manufactured, discrete size-isolated bubbles with a 1,2-Distearoyl-sn-glycero-3-phosphocholine (DSPC) and polyoxyethylene-40 stearate (PEG40S) shell and a perfluorobutane (PFB) gas core can induce BBB opening, adding to the group of pre-formed microbubbles capable of opening the BBB (e.g., in addition to Definity®, SonoVue®, and Optison™). Differential centrifugation, discussed above, was a key procedure, since it allowed for the production of large volumes of discrete size-isolated bubbles.

A typical size distribution for 1-2 μm and 4-5 μm diameter bubbles used in accordance with an exemplary embodiment, are depicted in FIG. 5(a) as the number-weighted and in FIG. 5(b) as the volume-weighted percentage of the total number of bubbles and gas volume, respectively. The solid lines in FIGS. 5(a)-(b) illustrate the size distribution of the two bubble size ranges prior to the BBB experiment, discussed further below, and the dashed lines indicate the distribution of size after the BBB experiment. As illustrated, in both instances, there was minimal size overlap between the two sets of bubbles. In the experiment discussed below, in order to test for stability, size distribution measurements were acquired from the same vial before the BBB opening and between 6 and 11 hours after the BBB opening experiments.

Table 1 illustrates the number-weighted and volume-weighted mean and median bubble sizes and polydispersity index (PI) for both sets of discrete size-isolated microbubbles. The PI, which was defined as the volume-weighted mean diameter divided by the number-weighted mean diameter, can be calculated to assess size uniformity. The 1-2 μm bubbles had number-weighted and volume-weighted mean and median diameters within the 1-2 μm range and a good PI value of 1.2±0.1 before the BBB opening experiments. After the experiment, the PI increased to 2.1±0.9, as indicated by the increased discrepancy between number-weighted and volume-weighted mean diameters. However, this distribution remained distinct in the 4-5 μm bubble set.

The 4-5 μm bubbles had volume-weighted mean and median values within the 4-5 μm range and a good PI value of 1.5±0.1. The number-weighted diameters were below the 4 μm target lower limit, but were still deemed distinct from the 1-2 μm bubble set. The volume-weighted diameter mean and median of the 4-5 μm range were 5.0±0.2 and 4.3±0.1, respectively. The bubble size distribution did not significantly change after the BBB opening experiments as indicated by the PI value of 1.4±0.1.

The stability of commercially available microbubbles has previously been characterized as stable over a period of at least two days. As illustrated in Table 1, the in-house manufactured bubbles discussed herein had a greater change in the Polydispersity Index (PI) over less than a day, but this could have been due to the fact that a large volume of bubbles were extracted from the vial with too little remaining for proper size distribution measurement with an Accusizer measurement device. As a result, after taking into account this potential artifact, the bubble's mean and median diameters did not necessarily change from before to after the BBB opening experiments as Table 1 seems to suggest. Regardless, even in the case where Table 1 indicated the actual maximum change in bubble diameter, the isolated peaks of bubbles remained distinct from one another, as illustrated in FIGS. 5(a) and 5(b).

TABLE 1

Summary of Microbubble Size Distribution

| | Number-weighted diameter (μm) | | Volume-weighted diameter (μm) | | |
|---|---|---|---|---|---|
| | (Mean ± SD) | (Median ± SD) | (Mean ± SD) | (Median ± SD) | PI |
| 1-2 μm bubbles | | | | | |
| Before experiment | 1.2 ± 0.1 | 1.2 ± 0.1 | 1.5 ± 0.2 | 1.5 ± 0.1 | 1.3 ± 0.1 |
| After experiment | 1.4 ± 0.2 | 1.3 ± 0.1 | 2.9 ± 1.5 | 2.6 ± 1.5 | 2.1 ± 0.9 |
| 4-5 μm bubbles | | | | | |
| Before experiment | 3.3 ± 0.1 | 3.4 ± 0.1 | 5.0 ± 0.2 | 4.3 ± 0.1 | 1.5 ± 0.1 |
| After experiment | 3.2 ± 0.2 | 3.2 ± 0.2 | 4.6 ± 0.4 | 4.3 ± 0.2 | 1.4 ± 0.1 |

The appropriate concentration of microbubbles can be determined 130 based on the nature of the subject 332, e.g., a human or a mouse, based on the size of the target region 440, e.g., the surface area of the BBB that one wishes to open, and based on the vessel size in the target region 440, e.g., 4-8 μm, or a combination of these factors. In the example of opening a BBB area on the order of millimeters, a concentration range of $10^7$ to $10^9$ bubbles/mL can be appropriate. In one exemplary embodiment, the total concentration for both size ranges of bubbles, e.g., 1-2 and 4-5 μm, was kept constant at approximately $8.5 \times 10^8$ number of bubbles per mL. In order to ensure accuracy of concentration, the bubbles were generated at an initial yield larger than the desired concentration and then diluted in PBS one minute before intravenous injection into the mouse.

In one exemplary embodiment, the bubble concentration can be chosen to be the same across different size distributions as opposed to the volume fraction, because it was assumed that BBB opening occurred discretely, e.g., the sites of molecular leakage highly correlated with the instantaneous locations of the bubbles at the time of sonication. This implied that BBB opening sites punctuated along the length of the capillaries. In the case where the volume fraction was kept the same for both sets of bubbles, it is deemed that the imaging protocol used would have the required sensitivity to detect minute increases in fluorescence.

Figure 6A:
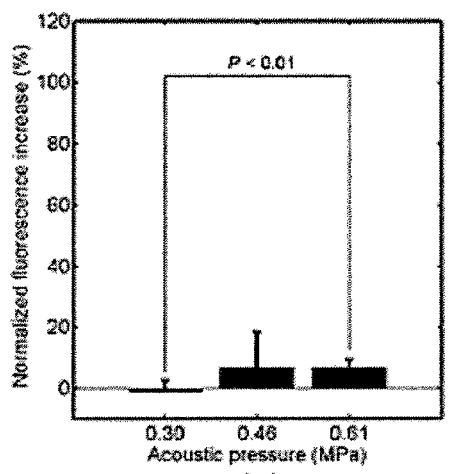
FIGS. 6(a)-(d) illustrate the increase in average fluorescence of a left brain region of interest relative to a right brain region of interest due to focused ultrasound sonication at different acoustic pressures and microbubble size ranges in accordance with an exemplary embodiment of the disclosed subject matter.
Figure 6B:
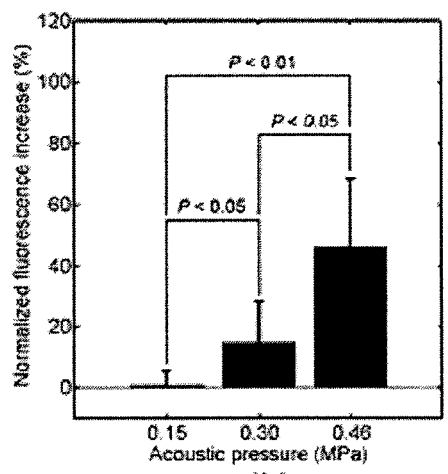
Figure 6C:
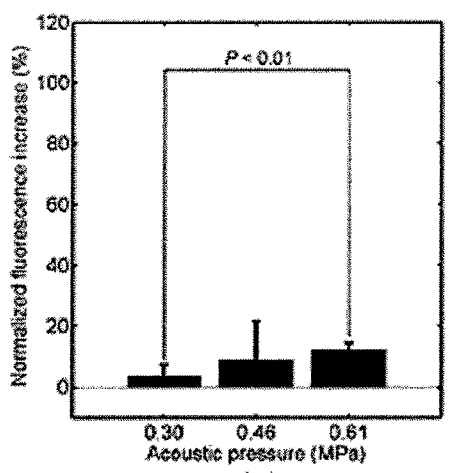
Figure 6D:
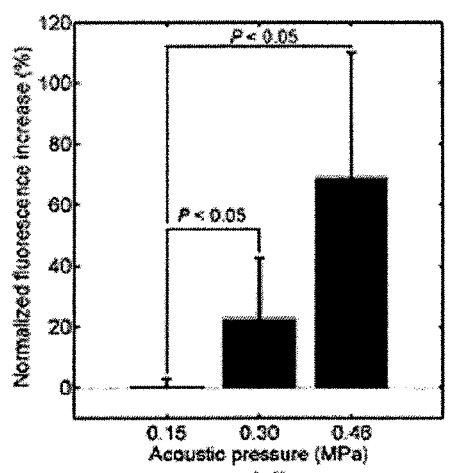

FIGS. 6(a)-(d) illustrate the increase in average fluorescence of the left region of interest (ROI) relative to the right ROI (the control) due to FUS sonication at different acoustic pressures and microbubble size ranges, in accordance with an exemplary experiment discussed below. FIGS. 6(a) and 6(b) illustrate the results where the hippocampi were the ROI and FIGS. 6(c) and 6(d) illustrate the results where the thalami was the ROI. FIGS. 6(a) and 6(c) illustrate the results using the 1-2 μm bubbles, while FIGS. 6(b) and 6(d) illustrate the results using the 4-5 μm bubbles. As illustrated in FIGS. 6(a) and 6(c), at 0.30 MPa, no increase in fluorescence in any of the mouse brains studied was detected. Although the overall concentration could have no effect on whether BBB opening occurs, it can have an effect on the number of BBB opening sites along the capillary length, and thus the amount of fluorescent-tagged dextrans infusing the parenchyma, e.g., the permeability. This can be a possible factor contributing to the 4-5 μm bubbles having greater fluorescence than 1-2 μm bubbles at a given pressure amplitude, as illustrated in FIGS. 6(b) and 6(d).

In one exemplary embodiment, the solution of microbubbles can be inserted 140 into the subject 332 such that the microbubbles make their way to the BBB of the subject 332. In one exemplary embodiment involving mice, a 25 μl bolus of the microbubble solution was injected 140 into the tail vein of the mouse 1 minute prior to sonication. In the example of a tissue that is outside the body of a subject 332, the solution of microbubbles can be position 140 in proximity to the target region by use of a syringe, or other appropriate device.

Following sonication, as described herein, the BBB opens, thereby facilitating the passage of a molecule through the BBB. Thus, a solution of contrast agent and/or other molecules (e.g., drugs) can be inserted 150 into the subject 332 such that it makes its way to the BBB and is able to pass through the same upon the opening of the BBB. The insertion 150 of the molecule into the subject 332 can occur prior to sonication, during sonication, or following sonication. Such molecule can be a drug, medication or pharmaceutical compound, protein, antibody or biological material, chemical substance, contrast agent, or any other material to pass through the BBB. In some embodiments, the molecule, whether a contrast agent, drug or other molecule, can be contained within a microbubble. In the same or another embodiment, the molecule can itself be composed of a microbubble. Further the molecule can be contained inside the microbubbles of the solution that is used to open the BBB or can itself be the same microbubbles. Such molecule can be inserted 150 into the subject 332 by any known method. For example, the molecule can be injected 150 into a vein of the subject. The molecule can also be administered 150 intraperitoneally by a catheter. In some embodiments, the molecule can be administered 150 orally. In the example of a tissue that is outside the body of a subject 332, the molecules can be positioned 150 in proximity to the target region by use of a syringe, or other appropriate device.

In some embodiments, an ultrasound can be applied 210 to image the opening of the BBB. For example, an ultrasound contrast agent can be administered 150 to the subject 332. Ultrasound scans 210 of the subject can be used to determine whether the BBB has opened. A bolus of ultrasound contrast agent, e.g., Optison™ containing microbubbles, can be injected into a vein of the subject 332 prior to sonication. In an exemplary embodiment, a 10 μL bolus (approximately 0.4 mL/kg) of Optison™ containing microbubbles having a mean diameter: 3.0 to 4.5 μm and a concentration of 5.0 to $8.0 \times 10^8$ bubbles per mL can be injected into the right femoral vein of the subject 332 fifteen minutes prior to sonication. High-resolution echocardiogram equipment can be used following sonication to determine the presence of the ultrasound contrast agent. Microbubbles containing material such as a contrast agent or a drug are administered to the subject 332 for traversal of the BBB.

An MRI contrast agent can also be administered 150 to the subject 332 for passage through the BBB. MRI scans can be used to monitor opening of the BBB. As illustrated in FIG. 3(a), in order to facilitate MRI scans during the procedure, an MRI system 350 can be incorporated into the equipment described hereinabove. T1- and T2-weighted MRI scans can be obtained using a 1.5 T, 3.0 T, 9.4 T, or other, system (Bruker Medical; Boston, Mass. USA). For example, 0.5 mL of MRI contrast agent gadolinium (Omniscan; Amersham Health, AS Oslo, Norway) can be administered 150 intraperitoneally via a catheter to depict BBB opening. Intraperitoneal injection 150 allows for the slow uptake of the MRI contrast agent into the bloodstream. After injection 150 of the MRI contrast agent, a series of scans 210 can be performed on the subject 332. For example, six alternating T1-weighted and T2-weighted fast spin-echo image scans 210, using the following specifications: a repetition time/echo time (TRITE) of 4000 ms/9.2 ms; rapid acquisition with relaxation enhancement: 16; field of view (FOV) of 1.92×1.92 cm; matrix size of 256×256; number of slices: 10; slice thickness: 0.6 mm; slice gap: 0.1 mm; number of excitations (NEX): 10, 15 and 45.

Contrast-enhanced behavior can be followed for a period of time after injection 150 of the contrast agent, to assess the time course of BBB opening. Detection of BBB opening can be detected (imaged) 210 by comparing an area of a nonsonicated homogeneous brain region with sonicated regions. Increased pixel intensity values of the sonicated regions which are increased above the values of the nonsonicated regions by a predetermined value, e.g., 2.5 standard deviations, are determined to be a contrast-enhanced region, revealing BBB opening. Higher resolution analysis can be used over an extended time period to determine the path of deposition of the molecule through the BBB.

The FUS transducer 302 supplies the focused ultrasonic waves to the targeted region 440. For example, pulsed-wave FUS can be applied in a series of bursts having delays between bursts. In an exemplary embodiment, the burst rate is about 1 to 20 Hz, the burst duration is 0.1 to 20 ms, and the duty cycle is 5-20%.

In some embodiments, the FUS acoustic pressure to be applied can be determined 160 based on size of the microbubbles compared to the size of the vessels in the target region 440 of the BBB such that the target value of opening is achieved. Exemplary acoustic pressures at the focus can be 0.15 to 3.0 MPa. In one example where the target value was such that 3 kDa molecules entered across an area on the order of 2 mm and utilizing 4-5 μm microbubbles at a concentration of $8.5 \times 10^8$ bubbles/mL, a pressure of 0.61 MPa was sufficient to acquire this target value. Other pressures fall within the range of 0.15-0.9 MPa. According to one embodiment, the FUS was applied in a series of five shots lasting, e.g., 10-40 ms each, with a delay between each shot of about 10-40 seconds. The FUS sonication procedure can be performed once or more on the subject's 332 brain. The actual output acoustic pressure values of the FUS transducer 302 can be calculated experimentally, for example, obtained from the values found in degassed water and corrected using the attenuation values of a skull similar to the subject's skull 401. Thus the FUS transducer 302 can be set at the proper level to produce the determined 160 pressure at the target region 440 of the subject's 332 brain.

In one example involving mice and as illustrated in FIGS. 6(a)-(d), the lowest peak-rarefactional pressure necessary for inducing BBB opening was 0.46 MPa for the 1-2 μm bubbles and 0.30 MPa for the 4-5 μm bubbles. The acoustic pressure threshold of BBB opening can be defined as the lowest pressure necessary for inducing BBB opening. Even though at 0.61 MPa there was significant BBB opening with the 1-2 μm bubbles, the fact that BBB opening was observed at 0.46 MPa for at least one mouse indicates that BBB opening can occur at this pressure amplitude. Thus in this exemplary embodiment, the acoustic pressure threshold for BBB opening fell between 0.30 and 0.46 MPa for the 1-2 μm bubbles and between 0.15 and 0.30 MPa for the 4-5 μm bubbles.

The rationale for the above-noted difference in acoustic pressure threshold can be based on the fact that cavitation and fragmentation threshold of microbubbles increases with decreasing vessel size. Changes in the bubble's resonance frequency and/or its constraint within a microvessel can be a factor in the increase in cavitation and fragmentation thresholds of microbubbles located in smaller vessels. It has previously been shown that commercially, non-size-isolated microbubbles are delivered both homogeneously across the BBB and concentrated near or along large vessels walls. However, when a small bubble (1-2 µm) flows in a capillary, it is not as constrained as a large bubble within that same environment. If the mechanical stress from the bubble against the vessel wall is the primary cause for BBB opening, then a high acoustic pressure amplitude will be necessary to induce this effect. Larger bubbles, given their comparable size (4-5 µm) to the capillary diameter (4-8 µm), can have higher inertial cavitation and fragmentation thresholds and persistence than if they were not as constrained by the vessel wall. Applying a low acoustic pressure to a bubble approximately the size of the microvessel can initiate stable bubble oscillations that induce stress against the wall as the bubble increases in size to fill the vessel. This mechanical stress can be high enough at 0.30 MPa to induce BBB opening for the 4-5 µm bubbles.

Accordingly, for bubbles that are not of a comparable size to the target region's vessels a higher pressure is necessary to induce the same degree of opening of the BBB. Thus, it is particularly advantageous to determine 120 the proper size range of microbubbles and to insert 140 a solution of discrete size-isolated microbubbles within the determined size range, as opposed to a solution of microbubbles that are not size-isolated, e.g., currently available polydispersed microbubbles.

Figure 6E:
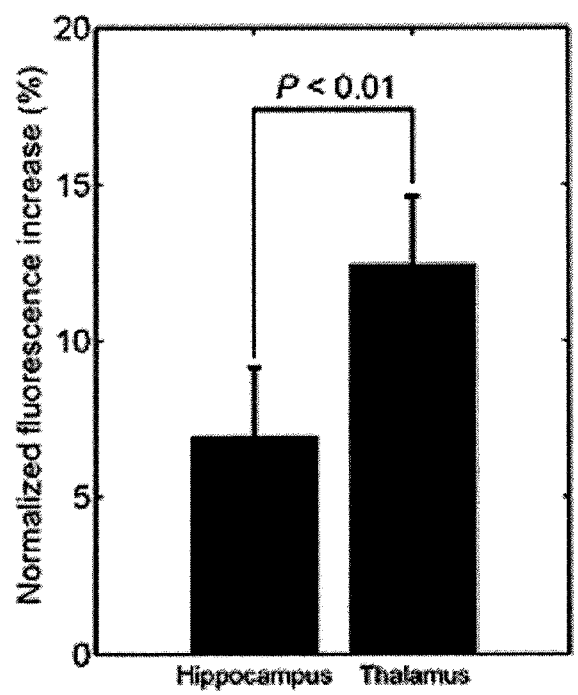
FIG. 6(e) illustrates an increase in average fluorescence of the left brain region of interest relative to the right brain region of interest due to focused ultrasound sonication at 0.61 MPa utilizing 1-2 µm microbubbles in accordance with an exemplary embodiment of the disclosed subject matter.

FIG. 6(e) illustrates the increase in average fluorescence of the left ROI relative to the right ROI due to FUS sonication at 0.61 MPa utilizing 1-2 µm bubbles. As illustrated in FIG. 6(e), the thalamus exhibits greater fluorescence, e.g., BBB opening, than the hippocampus. This could be due to the capillary density and/or the vascular architecture of the thalamus compared to the hippocampus. The higher number of capillaries, or sites of potential BBB opening, can be the cause for increased permeation of agents. Another possible rationale for the difference in fluorescence could be due to the fact that the extracellular space varies in terms of structure and diffusion rate, which implies differences in the rate of travel of delivered agents once they exit the vascular system.

EXAMPLE

Figure 7:
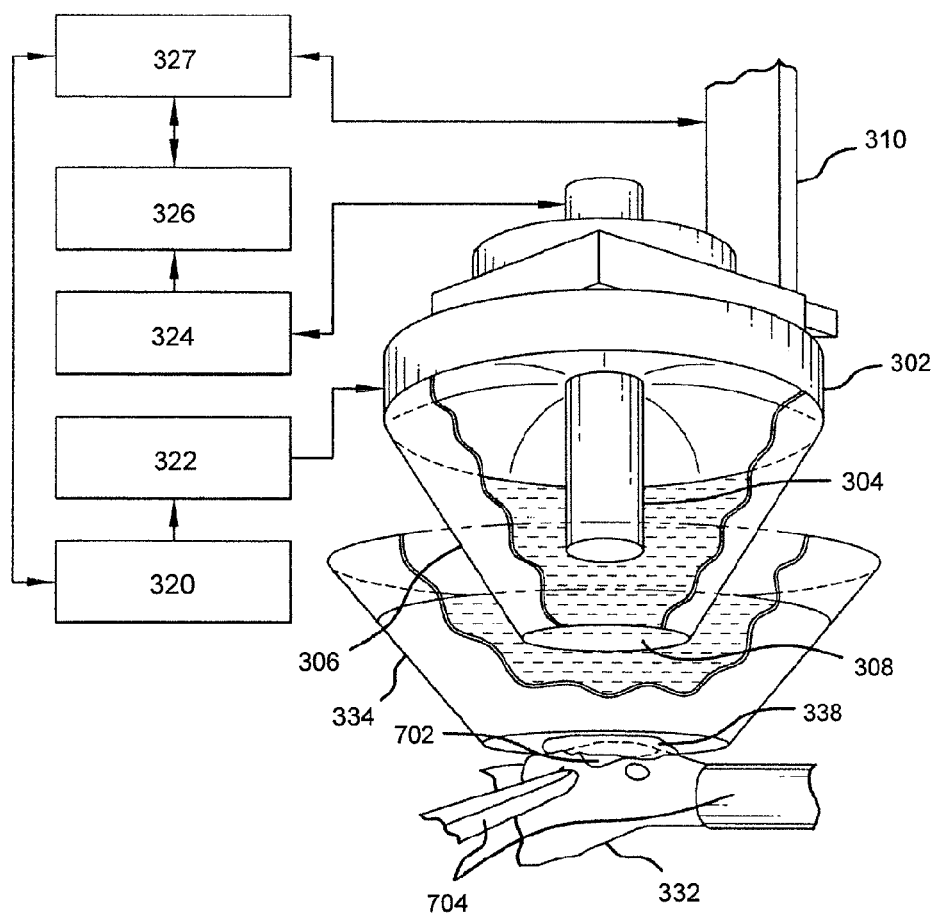
FIG. 7 illustrates a system for opening the blood-brain barrier used in connection with an experiment on mice in accordance with an exemplary embodiment of the disclosed subject matter.

FIG. 7 illustrates a system 300 used in an experiment, approved by the Columbia University Institutional Animal Care and Use Committee, on twenty-eight wild-type mice (strain: C57BL/6, mass: 28.0±4.5 g, sex: male; Harlan, Indianapolis, Ind., USA) which were studied in accordance with the techniques described herein. As illustrated in FIG. 7, the system 300 can include a FUS transducer 302, a pulse-echo diagnostic transducer 304, a cone 306, a latex membrane 308, a 3-D positioning system 310 all operatively connected to a function generator 320, a power amplifier 322, a pulse-receiver system 324, a digitizer 326 and a computer 327. The cone 306 can be inserted into a water container 334 which is sealed at the bottom by a polyurethane membrane 338 and placed on the shaved skull 702 of the mouse subject 332. The mouse subject 332 is held in place using a stereotaxic apparatus 704.

In the experiment, the mice were anesthetized using 1.25-2.50% isoflurane (SurgiVet, Smiths Medical PM, Inc., Wisconsin, USA) throughout both the BBB opening and transcardial perfusion procedures. After being anesthetized, each mouse 332 was placed prone with its head immobilized by the stereotaxic apparatus 704 (David Kopf Instruments, Tujunga, Calif., USA). The hair on the skull was removed using an electric trimmer and a depiatory cream. A degassed water-filled container 334 sealed at the bottom with thin, acoustically and optically transparent, Saran™ Wrap 338 (Saran™; SC Johnson, Racine, Wis., USA) was placed on top of the mouse head 702 while ultrasound coupling gel was used to eliminate any remaining impedance mismatch between the two surfaces. The FUS transducer 302 was then submerged in the water of the container 334 with its beam axis perpendicular to the surface of the skull 332.

The focus of the transducer was positioned inside the mouse brain using a grid-positioning method that utilized the pulse-echo diagnostic transducer 304, as discussed above. The grid was constructed from three 0.30 mm thin metal bars (i.e., paper clips) with two of the bars parallel to one another and separated by 4.00 mm. At the center of the parallel bars, and perpendicular to the two, was soldered the third bar. The grid was placed in the water bath 334, on top of the skull, and in alignment with sutures visible through the skin. The center bar was aligned along the sagittal suture and one of the parallel bars with the lambdoid suture. A lateral two-dimensional raster-scan of the grid using the diagnostic transducer was made and the transducer's beam axis was positioned 2.25 and 2.00 mm away from the sagittal and lambdoid suture, respectively. Finally, the focal point was placed 3.00 mm beneath the top of the skull so that the acoustic wave propagated through the left parietal bone and overlapped with the left hippocampus and a small portion of the lateral region of the thalamus. The right hippocampus was not targeted and was used as the control. The grid positioning method was sufficiently precise to have the FUS beam consistently overlap the hippocampus of the murine brain.

A 25 µl bolus of either the 1-2 or 4-5 µm diameter bubbles was injected into the tail vein 1 minute prior to sonication. For the 1-2 bubble set, pulsed FUS (pulse rate: 10 Hz, pulse duration: 20 ms, duty cycle: 20%) was applied at a set pressure of 0.30, 0.46, or 0.61 MPa peak-rarefactional in a series of two intervals consisting of 30-s of sonication at a single location (e.g., the hippocampus). Between each interval, a 30-s window allowed for residual heat between pulses to dissipate and microbubbles to reperfuse the cerebral vasculature undisturbed by the acoustic wave. The experiment was repeated for the 4-5 µm bubble set, but acoustic pressures were set at 0.15, 0.30, 0.46, or 0.61 MPa peak-rarefactional. The pressure ranges designated for the different bubble sets were roughly based on previous work with commercially available, non-size-isolated Definity® microbubbles. Since previous work has shown that the vascular characteristics (e.g., vascular density) in the sonicated region can influence the extent of BBB opening, the PUS sonication procedure was performed once and at a single location in each mouse brain in order to more accurately compare BBB opening pressure thresholds.

Approximately 10 min after FUS-induced BBB opening, 3 kDa Texas Red®-tagged dextrans were injected via the femoral vein. After a 20-min interval, which enabled the dextrans to circulate throughout the vasculature, the mice were transcardially perfused with 30 ml of phosphate buffer saline (138 mM sodium chloride, 10 mM phosphate, pH 7.4) and 60 ml of 4% paraformaldehyde. The brain was extracted from the skull and then post-fixed in paraformaldehyde overnight. Following the aforementioned procedures, the brain was prepared for either frozen (m=22) or paraffin sections (n=6). The frozen sectioning protocol provided an efficient means of analyzing fluorescence in order to determine the threshold for BBB opening. Meanwhile, the paraffin sections were used to analyze not only the presence of trans-BBB delivered dextrans, but also to assess for damage when sonicating at the pressure thresholds, e.g., 0.46 MPa with the 1-2 µm bubbles and 0.30 MPa with the 4-5 µm bubbles.

In preparation of frozen sectioning, the brain was cryoprotected by soaking it in 30% sucrose overnight. The brain was then embedded in a cutting temperature compound (Sakura Tissue-Tek O.C.T. Compound; Torrance, Calif., USA), frozen in a square mold, and then sectioned using a cryostat into 200 μm slices in the horizontal orientation. In preparation for paraffin sectioning the brain was embedded in paraffin. From the dorsal side of the brain, 1.2 mm was trimmed away. At the first level, 6 sections at 6 μm were obtained and placed on 3 slides. Then 80 μm were bypassed until the next level was sectioned. This was repeated for 12 levels for a total of 72 sections. At each level, the first two sections were stained with hematoxylin and eosin (H&E) while the latter four remained unstained and left for fluorescence imaging to detect the trans-BBB delivered dextrans.

Bright field and fluorescent images of the frozen sections were acquired using an inverted light and fluorescence microscope (IX-81; Olympus, Melville, N.Y., USA) at 4× magnification and with a motorized stage-scanner. Images of the paraffin sections were acquired using an upright light and fluorescence microscope (BX61; Olympus, Melville, N.Y., USA) at 4× and 10× magnification. In both cases, the Texas Red-tagged dextrans were excited at 568±24 nm while emissions were filtered for 610±40 nm.

In the case of the frozen sections, horizontal sections were chosen at defined cross-sections of the hippocampus, as depicted in FIGS. 8(a)-(f) (the 1-2 μm bubbles) and FIGS. 9(a)-(h) (the 4-5 μm bubbles). As illustrated in FIGS. 8 and 9, a 3×3 mm$^2$ region of interest (ROI) in the bright field images was selected using Adobe® Photoshop® CS2 (San Jose, Calif., USA) and the hippocampus and thalamus were manually outlined within this ROI. The outlines were then loaded into MATLAB® 2007 (Natick, Mass., USA) and used to isolate the hippocampus in the fluorescent images. The relative increase in fluorescence was then calculated by subtracting the spatially averaged fluorescence in the right ROI from the spatially averaged fluorescence in the left ROI and then dividing the resulting value by the spatially averaged fluorescence in the right ROI.

Differences between the two sets of values were determined using statistical analysis. Following the calculation of the mean and standard deviation in the change of fluorescence of the left over the right hippocampus for the five sets of values, a Students's t-test was performed. The same comparison amongst the five sets of values for the increase in area of fluorescence was made. In all comparisons, a difference in fluorescence at $P<0.05$ was considered statistically significant (FIGS. 6(a)-(d)).

Figures 8A, 8B, 8C, 8D, 8E, 8F:
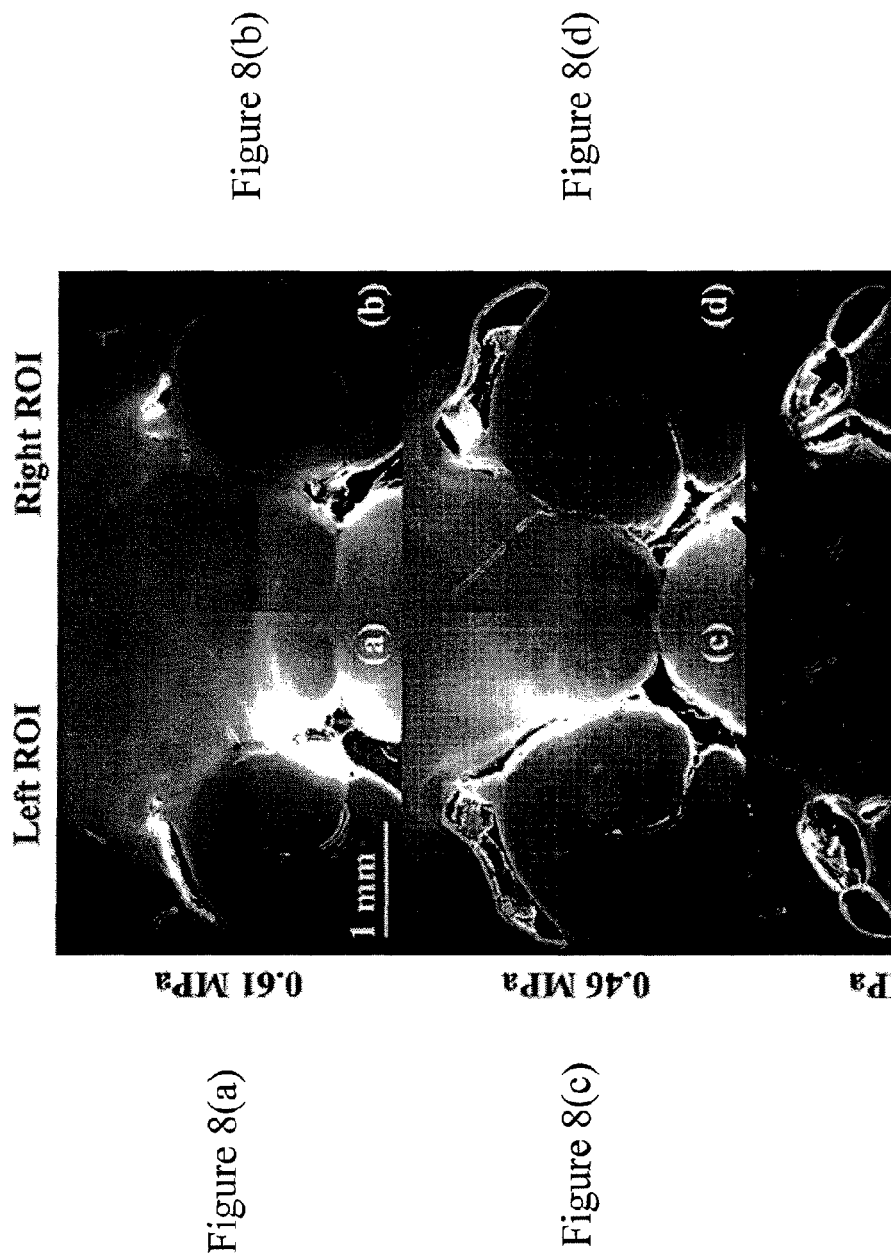
FIGS. 8(a)-(f) illustrate fluorescence images of three different mouse brains after injection of 1-2 µm microbubbles, sonication at three different acoustic pressures (0.30, 0.46 and 0.61 MPa) and subsequent injection of fluorescent-tagged dextrans of 3 kDa in accordance with an exemplary embodiment of the disclosed subject matter.

As noted above, FIGS. 8(a)-(f) illustrate fluorescence images of three different mouse brains after injection of 1-2 μm bubbles, sonication at three different acoustic pressures (0.30, 0.46 and 0.61 MPa) and subsequent injection of fluorescent-tagged dextrans of 3 kDa. FIGS. 8(a), 8(c) and 8(e) (the left ROI) illustrate the left hippocampus and thalamus which were FUS sonicated, while FIGS. 8(b), 8(d) and 8(f) illustrate the right hippocampus and thalamus which were not sonicated (the right ROI).

As illustrated in FIGS. 8(a)-(f), following the systemic injection of 1-2 μm bubbles, FUS sonication induced an increase in fluorescence at 0.46 and 0.61 MPa (FIGS. 8(a), 8(c)) while no fluorescence increase was observed at 0.30 Mpa (FIG. 8(e)). At 0.46 MPa, increased fluorescence was predominant in the hippocampal fissure and the fissure between the hippocampus and thalamus. However, fluorescence in these regions was not included in the outline of either the hippocampus or thalamus since they do not have extensive capillary networks and are situated near large vessels. Although increases in fluorescence were observed in regions with a more homogeneous distribution of capillaries (i.e., no large vessels), it was not consistent across enough mice to unequivocally indicate BBB opening and resulted in a wide variation in the increase in fluorescence ($P>0.1$; FIG. 6(a), (b)). However, a statistically significant increase was observed at 0.61 MPa, as illustrated in FIGS. 6(a) and 6(b).

As noted above, FIGS. 9(a)-(h) illustrate fluorescence images of three different mouse brains after injection of 4-5 μm bubbles, sonication at four different acoustic pressures (0.16, 0.30, 0.46 and 0.61 MPa) and subsequent injection of fluorescent-tagged dextrans of 3 kDa. FIGS. 9(a), 9(c), 9(e) and 9(g) (the left ROI) illustrate the left hippocampus and thalamus which were FUS sonicated, while FIGS. 9(b), 9(d), 9(f) and 9(h) illustrate the right hippocampus and thalamus which were not sonicated (the right ROI).

Figures 9A, 9B, 9C, 9D, 9E, 9F, 9G, 9H:
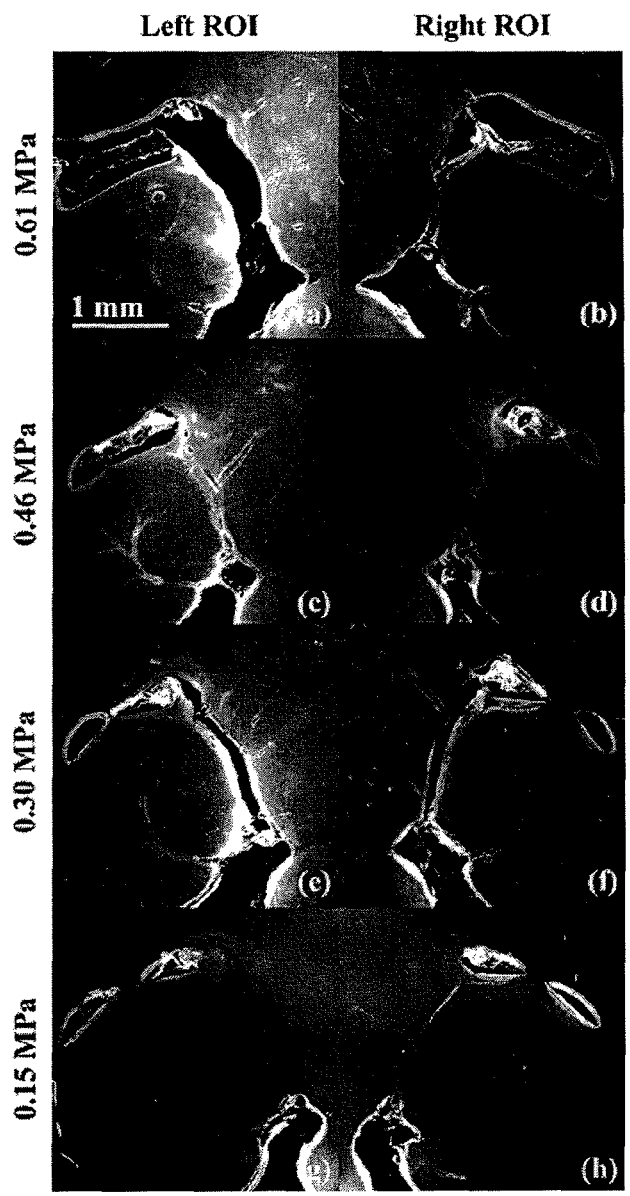
FIGS. 9(a)-(h) illustrate fluorescence images of three different mouse brains after injection of 4-5 µm microbubbles, sonication at four different acoustic pressures (0.16, 0.30, 0.46 and 0.61 MPa) and subsequent injection of fluorescent-tagged dextrans of 3 kDa in accordance with an exemplary embodiment of the disclosed subject matter.

As illustrated in FIGS. 9(a)-(h), following the systemic injection of 4-5 μm bubbles, FUS sonication induced an increase in fluorescence at 0.30, 0.46 and 0.61 MPa (FIGS. 9(a), (c), and (e)) that were statistically significant ($P<0.05$) while no fluorescence increase was observed at 0.15 MPa (FIG. 9(g)). At 0.30 MPa and above, fluorescence was observed not only at the fissures and along large vessels, but diffusely through the hippocampus and thalamus. A statistically significant increase in fluorescence in the hippocampus was detected between 0.30 and 0.46 MPa.

For each ROI and acoustic pressure, 4-5 μm bubbles produced greater increases in fluorescence compared to the 1-2 μm bubbles. In addition, the peak negative pressure amplitude threshold where significant fluorescence was observed was lower for the 4-5 μm bubbles than for the 1-2 μm bubbles. This implies that a lower acoustic pressure is required to induce BBB opening for the larger 4-5 μm bubbles.

It was qualitatively noted that there were regional variations in fluorescence within the sonicated region (FIGS. 8(a), (c)). Therefore a comparison of the enhancement in fluorescence in the thalamus and hippocampus at 0.61 MPa and with 1-2 μm bubbles was performed. As illustrated in FIG. 6(e), a clear difference in the increase in fluorescence was detected ($P<0.01$).

Six mouse brains were assessed for histological damage as defined by the presence of discrete damage sites, such as neuronal damage (dark neurons), gross hemorrhage, vacuolization, and small erythrocyte extravasations. Three of the six mice were sonicated at 0.46 MPa in the presence of 1-2 μm bubbles while the other three were sonicated at 0.30 MPa in the presence of 4-5 μm bubbles. No discrete sites of hemorrhage were detected in the twelve slices analyzed at level sections 1, 6, 8, 10, and 12.

Figure 10A:
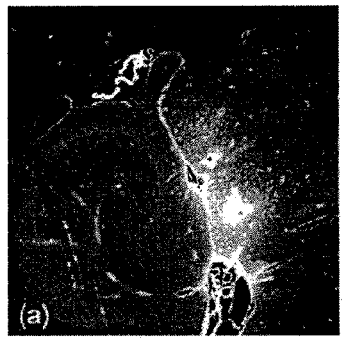
FIGS. 10(a)-(f) illustrate histological images of a mouse brain after injection of 1-2 µm microbubbles and focused ultrasound sonication at 0.46 MPa in accordance with an exemplary embodiment of the disclosed subject matter.
Figure 10B:
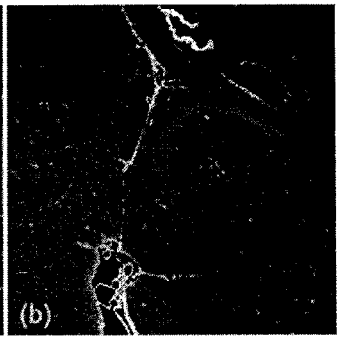
Figure 10C:
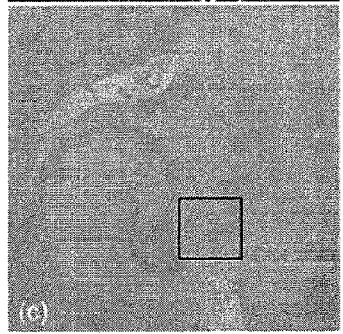
Figure 10D:
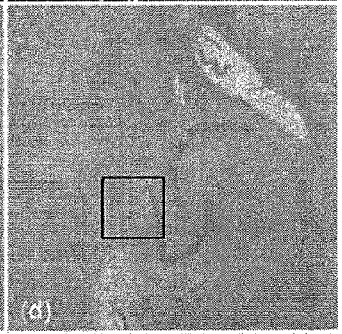
Figure 10E:
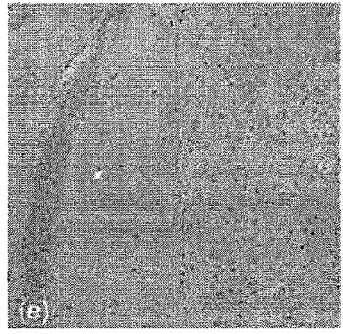
Figure 10F:
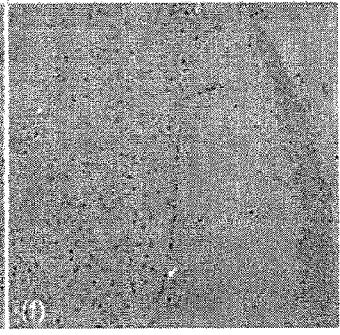

FIGS. 10(a)-(f) illustrate histological images of a mouse brain after injection of 1-2 μm bubbles and sonicated at 0.46 MPa (6-μm thick fluorescent unstained and H&E-stained slices that were sequentially sectioned), with FIGS. 10(a), 10(c) and 10(e) illustrating the left hippocampal and thalamic regions which were sonicated and FIGS. 10(b), 10(d) and 10(f) illustrating the right hippocampal and thalamic regions which were not sonicated. FUS sonication in the presence of 1-2 μm bubbles clearly depicts BBB opening at 0.46 MPa, as illustrated by comparing FIG. 10(a) with 10(b). The sections directly above those depicted in FIGS. 10(a) and 10(b) were H&E-stained and are illustrated in FIGS. 10(c) and 10(d), which are 4× magnifications. FIGS. 10(e) and 10(f) are 10× magnifications which illustrate the ROI's indicated by the black boxes in FIGS. 10(c) and 10(d). As can be seen in FIGS. 10(c)-(f), no discrete damage sites were observed. In some sections (FIG. 10(e)), erythrocytes were qualitatively observed (small white arrows), but they also appeared in the control, contralateral hemisphere (FIG. 10(f)), thus indicating that this might be due to histological artifacts rather than damage cause by the FUS sonication. In addition, it was difficult to determine whether these erythrocytes remained within vessels or whether they had extravasated.

Figure 11A:
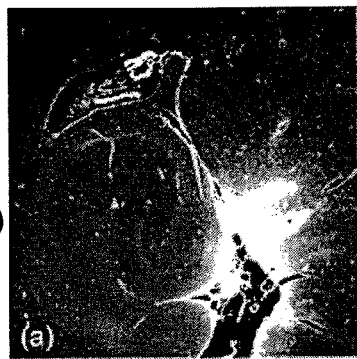
FIGS. 11(a)-(f) illustrate histological images of a mouse brain after injection of 4-5 µm bubbles and focused ultrasound sonication at 0.30 MPa in accordance with an exemplary embodiment of the disclosed subject matter.
Figure 11B:
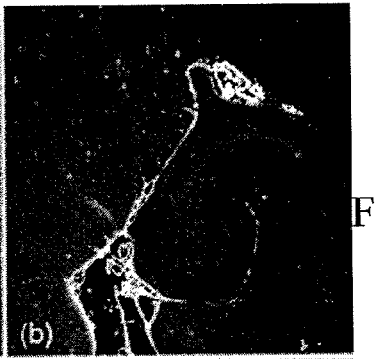
Figure 11C:
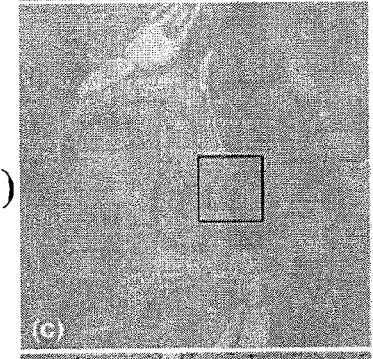
Figure 11D:
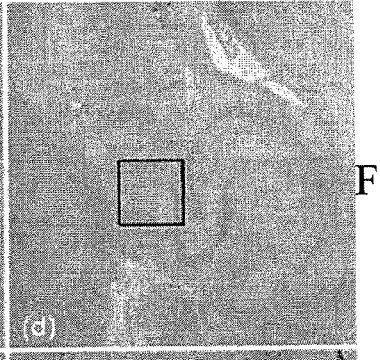
Figure 11E:
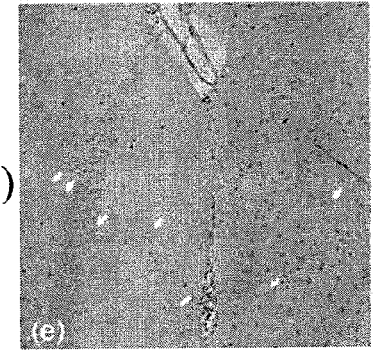
Figure 11F:

FIGS. 11(a)-(f) illustrate histological images of a mouse brain after injection of 4-5 μm bubbles and sonicated at 0.30 MPa (6-μm thick fluorescent unstained and H&E-stained slices that were sequentially sectioned), with FIGS. 11(a), 11(c) and 11(e) illustrating the left hippocampal and thalamic regions which were sonicated and FIGS. 11(b), 11(d) and 11(f) illustrating the right hippocampal and thalamic regions which were not sonicated. FUS sonication at 0.30 MPa in the presence of 4-5 μm bubbles also resulted in BBB opening, as illustrated by comparing FIGS. 11(a) with 11(b). As with the 1-2 μm range depicted in FIGS. 10(c) and 10(d), the 4-5 μm range illustrated in FIGS. 11(c) and 11(d) (at 4× magnification and H&E-stained) shows no discrete damage sites due to the FUS sonication. Small erythrocyte extravasations were observed (as indicated by white arrows) on both the sonicated and control hemispheres, as illustrated in FIGS. 11(e) and 11(f) (at 10× magnification of the black box ROI's in FIGS. 10(c), (d)).

As FIGS. 10(e), 10(f), 11(e) and 11(f) illustrate, for the respective minimum pressures and bubbles tested, regions where a high intensity of fluorescence was observed were not associated with any dead neurons, necrotic sites, or hemorrhaging, thus confirming the safety and efficacy of using discrete size-isolated microbubbles to effectuate the opening of the blood-brain barrier as discussed herein.

It will be understood that the foregoing is only illustrative of the principles described herein, and that various modifications can be made by those skilled in the art without departing from the scope and spirit of the disclosed subject matter. For example, the system and methods described herein are used for opening the blood-brain barrier of a subject. It is understood that techniques described herein are useful for opening of any vascular tissue. Further, the techniques described have been performed on mice but it is understood the techniques are applicable to other subject, such as humans. Moreover, features of embodiments described herein can be combined and/or rearranged to create new embodiments.

We claim:

1. A method for opening a tissue to a target value, comprising:
    targeting a region of said tissue for opening;
    selecting the target value based on a size of a molecule to pass through the tissue and a surface area of the region to be exposed to the molecule;
    determining a size range of microbubbles corresponding to said target value;
    generating a polydispersed microbubble distribution using acoustic emulsification;
    isolating the microbubbles of the size range from the polydispersed microbubble distribution using differential centrifugation;
    positioning the microbubbles of said size range in proximity to said targeted region; and
    applying an ultrasound beam to said targeted region such that said tissue is opened with the assistance of said microbubbles to said target value.

2. The method of claim 1, further comprising determining a concentration range of microbubbles corresponding to said target value, and wherein positioning said microbubbles further comprises positioning said microbubbles of said concentration range.

3. The method of claim 1, further comprising determining a pressure range for said ultrasound beam corresponding to said target value, and wherein applying said ultrasound beam comprises applying said ultrasound beam at said pressure range.

4. The method of claim 3, wherein said pressure range corresponds to a resonance frequency of said microbubbles proximate to said targeted region.

5. The method of claim 1, wherein said tissue comprises a blood-brain barrier.

6. The method of claim 1, wherein said tissue comprises a vessel.

7. The method of claim 1, further comprising applying an ultrasound beam to move said microbubbles into vessels of said tissue.

8. The method of claim 1, wherein determining said size range of microbubbles comprises determining a size range corresponding to a size range of vessels of said tissue.

9. The method of claim 1, wherein said size range of microbubbles is 4 to 5 microns.

10. The method of claim 1, wherein said size range of microbubbles is 1 to 2 microns.

11. The method of claim 1, wherein said size range of microbubbles is 9 to 10 microns.

12. The method of claim 1, wherein said size range of microbubbles is 6 to 8 microns.

13. The method of claim 1, wherein said microbubbles are acoustically activated microbubbles.

14. The method of claim 1, wherein said microbubbles are molecule carrying microbubbles.

15. The method of claim 14, wherein said molecule is a medicinal molecule.

16. The method of claim 14, wherein said molecule is a contrast agent.

17. The method of claim 14, wherein said molecule is a biomarker.

18. The method of claim 14, wherein said molecule is a liposome.

19. The method of claim 14, wherein said molecule carrying microbubbles are carrying a medicinal molecule and a contrast agent.

20. The method of claim 1, further comprising positioning medicinal molecules in proximity to said targeted region.

21. The method of claim 1, further comprising positioning a contrast agent in proximity to said targeted region.

22. The method of claim 1, wherein the desired permeability comprises one or more of a size of a molecule to pass through the tissue, an area of the tissue to be opened, and a rate at which molecules pass through the tissue.

23. A method for imaging the opening of a tissue to a target value, comprising:
    targeting a region of said tissue for opening;
    selecting the target value based on a size of a molecule to pass through the tissue and a surface area of the region to be exposed to the molecule;
    determining a size range of microbubbles corresponding to said target value;
    generating a polydispersed microbubble distribution using acoustic emulsification;
    isolating the microbubbles of the size range from the polydispersed microbubble distribution using differential centrifugation;
    positioning the microbubbles of said size range in proximity to said targeted region;
    applying an ultrasound beam to said targeted region such that said tissue is opened with the assistance of said microbubbles to said target value; and collecting image information for said targeted region of said opening tissue.

24. The method of claim 23, wherein imaging said targeted region comprises applying an ultrasound beam to said targeted region.

25. The method of claim 23, wherein imaging said targeted region comprises utilizing a magnetic resonance imaging device to image said targeted region.

26. A system for opening a tissue to a target value, comprising:
   a targeting assembly for targeting a region of said tissue;
   a processor programmed with logic configured to:
      select the target value based on a size of a molecule to pass through the tissue and a surface area of the region to be exposed to the molecule; and
      determine a size range of microbubbles corresponding to said target value;
   a probe adapted to generate a polydispersed microbubble distribution using acoustic emulsification;
   a centrifuge adapted to isolate the microbubbles of the size range from the polydispersed microbubble distribution using differential centrifugation; and
   an introducer adapted to deliver a solution including the microbubbles of the size range to a location proximate to said targeted region; and
   a transducer, coupled to said targeting assembly, adapted to apply an ultrasound beam to said targeted region to thereby open said tissue with the assistance of said microbubbles to said target value.

27. The system of claim 26, wherein the system comprises an imaging transducer.

28. The system of claim 26, wherein said targeting assembly comprises one or more members for placement on an anatomical landmark of said tissue.

29. The system of claim 26, wherein said solution of size-controlled microbubbles further comprises a microbubble concentration range corresponding to said target value.

30. The system of claim 26, wherein said solution of size-controlled microbubbles further comprise microbubbles of a size range corresponding to a size range of vessels of said tissue.

31. The system of claim 26, wherein said tissue comprises a blood-brain barrier.

32. The system of claim 26, wherein said tissue comprises a vessel.

33. The system of claim 26, wherein said size range of microbubbles is 4 to 5 microns.

34. The system of claim 26, wherein said size range of microbubbles is 1 to 2 microns.

35. The system of claim 26, wherein said size range of microbubbles is 9 to 10 microns.

36. The system of claim 26, wherein said size range of microbubbles is 6 to 8 microns.

37. The system of claim 26, wherein said microbubbles are acoustically activated microbubbles.

38. The system of claim 26, wherein said microbubbles are molecule carrying microbubbles.

39. The system of claim 38, wherein said molecule is a medicinal molecule.

40. The system of claim 38, wherein said molecule is a contrast agent.

41. The system of claim 38, wherein said molecule is a biomarker.

42. The system of claim 38, wherein said molecule is a liposome.

43. The system of claim 38, wherein said molecule carrying microbubbles are carrying a medicinal molecule and a contrast agent.

44. The system of claim 38, wherein said molecule carrying microbubbles are coated with a medicinal molecule and a contrast agent.

45. The system of claim 26, further comprising a solution of medicinal molecules and an introducer for delivering said solution of medicinal molecules to a location proximate to said targeted region.

46. The system of claim 26, further comprising a solution of contrast agent and an introducer for delivering said solution of contrast to a location proximate to said targeted region.

47. A system for imaging the opening of a tissue to a target value, comprising:
   a targeting assembly for targeting a region of said tissue;
   a data processor programmed with logic configured to:
      select the target value based on size of a molecule to pass through the tissue and a surface area of the region to be exposed to the molecule; and
      determine a size range of microbubbles corresponding to said target value;
   a probe adapted to generate a polydispersed microbubble distribution using acoustic emulsification;
   a centrifuge adapted to isolate the microbubbles of the size range from the polydispersed microbubble distribution using differential centrifugation;
   an introducer adapted to deliver a solution including the microbubbles of the size range to a location proximate to said targeted region; and
   a transducer, coupled to said targeting assembly, adapted to apply an ultrasound beam to said targeted region to thereby open said tissue with the assistance of said microbubbles to said target value;
   an imaging device adapted to capture image data of said opened tissue of said targeted region; and
   an image processor, operatively coupled to said imaging device, adapted to process said image data to form an image therefrom.

48. The system of claim 47, wherein said imaging device comprises an imaging transducer.

49. The system of claim 47, wherein said imaging device comprises a magnetic resonance imaging device.

50. The system of claim 47, wherein said imaging device comprises an optical imaging device.

* * * * *